(12) United States Patent
Blainey et al.

(10) Patent No.: US 12,060,391 B2
(45) Date of Patent: Aug. 13, 2024

(54) CONSTRUCTS FOR CONTINUOUS MONITORING OF LIVE CELLS

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); Jacob Borrajo, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 30 days.

(21) Appl. No.: 15/558,497

(22) PCT Filed: Mar. 16, 2016

(86) PCT No.: PCT/US2016/022722
§ 371 (c)(1),
(2) Date: Sep. 14, 2017

(87) PCT Pub. No.: WO2016/149426
PCT Pub. Date: Sep. 22, 2016

(65) Prior Publication Data
US 2018/0079786 A1    Mar. 22, 2018

Related U.S. Application Data

(60) Provisional application No. 62/133,551, filed on Mar. 16, 2015.

(51) Int. Cl.
| | | |
|---|---|---|
| C12N 15/63 | (2006.01) | |
| A61K 39/21 | (2006.01) | |
| C07K 14/005 | (2006.01) | |
| C07K 14/16 | (2006.01) | |
| C12N 7/04 | (2006.01) | |
| C12N 15/85 | (2006.01) | |

(52) U.S. Cl.
CPC ........... *C07K 14/16* (2013.01); *A61K 39/21* (2013.01); *C07K 14/005* (2013.01); *C12N 7/04* (2013.01); *C12N 2740/16023* (2013.01); *C12N 2740/16222* (2013.01)

(58) Field of Classification Search
None
See application file for complete search history.

(56) References Cited

U.S. PATENT DOCUMENTS 6,451,304 B1    9/2002   Friedmann et al.
6,709,814 B1*   3/2004   Anderson .............. C07K 14/47
                                                    435/7.1
8,119,145 B2    2/2012   Vajdy et al.
8,841,438 B2    9/2014   Tenenbaum et al.
2005/0123563 A1* 6/2005  Doranz .............. A61K 47/6901
                                                    424/204.1
2011/0027267 A1  2/2011  Kyneb et al.
2014/0004146 A1  1/2014  Zhou et al.

FOREIGN PATENT DOCUMENTS

| WO | 2010059689 A2 | 5/2010 |
| WO | 2010083532 A1 | 7/2010 |
| WO | 2011094617 A2 | 8/2011 |
| WO | 2013068847 A2 | 5/2013 |
| WO | 2013174999 A1 | 11/2013 |

OTHER PUBLICATIONS

Canton et al. (Nature Reviews 2013, vol. 13, pp. 621-634).*
International Search Report and Written Opinion for PCT Application No. PCT/US2016/022722, Jun. 24, 2016, 15 pages.
"International Preliminary Report on Patentability for PCT Application No. PCT/US2016/022722", Sep. 19, 2017, 1-10.
Cai, et al., "Frequency-Modulated Nuclear Localization Bursts Coordinate Gene Regulation", Nature, vol. 455, No. 7212, Sep. 25, 2008, 485-490.
Gopal, et al., "Visualizing large RNA molecules in solution", RNA (2012) 18:284-299
Picelli, et al., "Full-Length RNA-Seq From Single Cells Using Smart-seq2", Nature Protocols, vol. 9, No. 1, 2014, 171-181.
Rein, et al., "Diverse Interactions of Retroviral Gag Proteins With RNAs", Trends Biochem Sci. Jul. 2011; 36(7): 373-380. doi:10.1016/j.tibs.2011.04.001.
Siwiak, et al., "Transimulation—Protein Biosynthesis Web Service", PLoS One, Sep. 2013, vol. 8, Issue 9, 8 pages.
Yang, et al., "Decay Rates of Human mRNAs: Correlation with Functional Characteristics and Sequence Attributes", Genome Research, vol. 13, No. 8, Aug. 2003, 1863-1872.
Yosef, et al., "Dynamic Regulatory Network Controlling Th17 Cell Differentiation", Nature, vol. 496, No. 7446, Apr. 25, 2013, 461-468.
Yosef, et al., "Impulse control: Temporal dynamics in gene transcription", Cell. Mar. 18, 2011; 144(6): 886-896.

* cited by examiner

*Primary Examiner* — Celine X Qian
(74) *Attorney, Agent, or Firm* — F. Brent Nix, Esq.; Johnson, Marcou, Isaacs & Nix, LLC

(57) ABSTRACT

Embodiments disclosed herein provide nucleic acid constructs and methods of use thereof that induce a live cell to give off sub-samples of the cell's cytosolic content. The tem "cell" as used herein may be any cell type. In certain example embodiments, the cells are mammalian cells. The sampling can be general or can be targeted to a particular class of molecules or to specific types of molecules. The constructs facilitate generation of a read-out for high-throughput screens by combining engineered export with simple bulk sample and sample processing. Live cell sampling enables time course measurements and expands, for example, the applicability of transcriptional profiles obtained by single cell gene expression analysis.

26 Claims, 18 Drawing Sheets
Specification includes a Sequence Listing.

| reporting unit scale | typical number of cells in reporting unit | sample collection time to accumulate 10 detected counts of a given mRNA, protein, or lipid species* | | |
|---|---|---|---|---|
| | | example RNA species present at 1000 copies per cell (assume total of 200,000 mRNA/cell) | example protein species present at 0.05% in VLP sample | example lipid species present at 0.05% in VLP sample |
| Single Cell | 1 | hours | :: | :: |
| Tissue | 50,000 | seconds | seconds | seconds |
| Organ | 10,000,000 | very short | very short | very short |
| Organism | 1x10$^{11}$ | very short | very short | very short |
| Total molecules samples per cell per hour | | 3,000 | 100,000 | 1,000,000 |
| estimated % of cell's production | | 10% | <1% | <5% |
| estimated analytical detection efficiency | | 10% | 0.1% | 0.1% |

* equivelant to assay time resolution for quantification with coefficient of variation ~30%

FIG. 18

CONSTRUCTS FOR CONTINUOUS MONITORING OF LIVE CELLS

The present application is a 35 U.S.C. § 371 national stage application of International Patent Application No. PCT/US2016/022722 filed on Mar. 16, 2016, which claims the benefit of U.S. Provisional Patent Application No. 62/133,551 filed Mar. 16, 2015. The entire contents of the above-referenced applications are hereby incorporated in their entirety herein.

TECHNICAL FIELD

The subject matter disclosed herein is generally related to nucleic acid constructs for continuous monitoring of live cells. Specifically, the subject matter disclosed herein is directed to nucleic acid constructs that encode secretion-inducing proteins that induce live cells to self-report cellular contents while maintaining cell viability.

BACKGROUND

Single-cell gene expression (SCGE) profiling is an important analytical technique for the study of mammalian cells. The ability to obtain highly resolved molecular phenotypes directly from individual cells is transforming the way cell states are defined, cell circuitry is understood, and cellular responses to environmental cues are studied. There is tremendous interest in moving beyond static snapshots of SCGE in cell suspensions to understand how SCGE profiles change over time. Technology that reports the internal state and functional history of cells within tissues would enable novel insight into dynamic biological processes. Current SCGE profiling technology addresses static heterogeneity (e.g., a snapshot of differences among single cells). However, dynamic signaling processes (Cai L, Nature 2008; Yosef N, Cell 2011; Yosef N, Nature 2013) and transitions in cell type and function over time are crucial to cellular biology and organism-level function. Enabling the comprehensive study of dynamic processes at the single-cell level is of intense interest, but tools for non-destructive in situ analysis are currently lacking. New non-destructive methods are needed to obtain multiple information-rich samples at different time points from the same living cell.

SUMMARY

In one aspect, the embodiments described herein are directed to nucleic acid constructs encoding a secretion-inducing protein. When expressed in live cells, the secretion inducing protein induces the cells to export samples of cellular contents that can be readily isolated and analyzed while maintaining cell viability. In certain example embodiments, the secretion inducing protein self-assembles to form an export compartment that packages cellular contents inside the export compartment for export from the cell. In certain other example embodiments, the secretion-inducing protein is a viral capsid or coat protein that self-assembles into a virus like particle and packages cellular contents for export from the cell. In certain example embodiments, the viral capsid protein is a Gag protein.

In another aspect, the embodiments described herein are directed to nucleic acid constructs that express a fusion protein, the fusion protein comprising a secretion-inducing domain and an affinity domain. The secretion-inducing domain may comprise the secretion-inducing proteins referenced above. The affinity domain allows for more targeted packaging of cellular contents by binding a particular class of cellular molecules or sub-types of a particular class of cellular molecules. For example, the affinity domain may bind all cellular RNA, one cellular RNA, or an exogenously introduced RNA. The affinity element may bind small molecules, carbohydrates, lipids, proteins, or nucleic acids. In certain example embodiments, the affinity domain may bind another molecule, such as an antibody or aptamer, that binds small molecules, carbohydrates, lipids, proteins, or nucleic acids. In certain example embodiments, the fusion protein comprises a Gag protein and a RNA-binding protein. In certain example embodiments, the RNA-binding protein is a poly-A binding protein (PABP).

The nucleic acid constructs described herein may further comprise an inducible promoter to control expression of the secretion-inducing protein and/or fusion protein. The nucleic acid constructs described herein may further comprise a steric linker. The steric linker may control the rate of secretion, the size of compartments formed by the secretion-inducing protein, or both.

In another aspect, the embodiments disclosed herein comprise vectors comprising the nucleic acid constructs described herein. In certain example embodiments, the vectors are viral vectors. In certain other example embodiments, the vectors are non-viral vectors.

In another aspect, the embodiments disclosed herein comprise methods for continuous monitoring of level cells comprising delivering into one or more cells a nucleic acid construct encoding a secretion-inducing protein; expressing the nucleic acid construct where expression of the secretion-inducing protein in the one or more cells results in the export of cellular contents in association with the secretion-inducing proteins; and isolating the exported cellular contents.

In another aspect, the embodiments disclosed herein comprise methods for continuous monitoring of live cells comprising delivering into one or more cells a nucleic acid construct encoding a fusion protein, the fusion protein comprising a secretion-inducing domain and an affinity domain; expressing the nucleic acid construct in the one or more cells, wherein expression of the fusion protein in the one or more cells results in the export of cellular contents; and isolating the exported cytosolic contents at one or more time points. In certain example embodiments, the secretion-inducing protein is a viral capsid protein and the affinity domain binds small molecules, carbohydrates, lipids, proteins, or nucleic acids. In one example embodiment, the secretion-inducing protein is a Gag protein. In another example embodiment, the affinity domain comprises a RNA binding protein. In certain example embodiments the RNA protein is PABP. In certain other example embodiments the RNA protein is an Argonaute protein.

In another aspect, embodiments disclosed herein include kits comprising the nucleic acid constructs and/or vectors described herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 18 is a table showing projected achievable time resolution using example embodiments described herein. The natural scale on which to measure perturbation is the mRNA production rate. For example, about 15% of the transcriptome is turned over per hour in mammalian cells, corresponding to about 30,000 molecules per hour per cell. If sampling happens below this rate using VLPs (roughly 3,000 molecules per hour per cell) it is believed that sampling will minimally perturb the state and function of the exporting cells. Such an export rate is sufficient to identify cell type and dynamics of highly expressed genes on the timescale of hours in individual cells. Higher time resolution or analysis of genes expressed at low levels will require a larger population of exporting cells or accepting lower time resolution, respectively.

DETAILED DESCRIPTION OF THE EXAMPLE EMBODIMENTS

Overview

Figure 1:
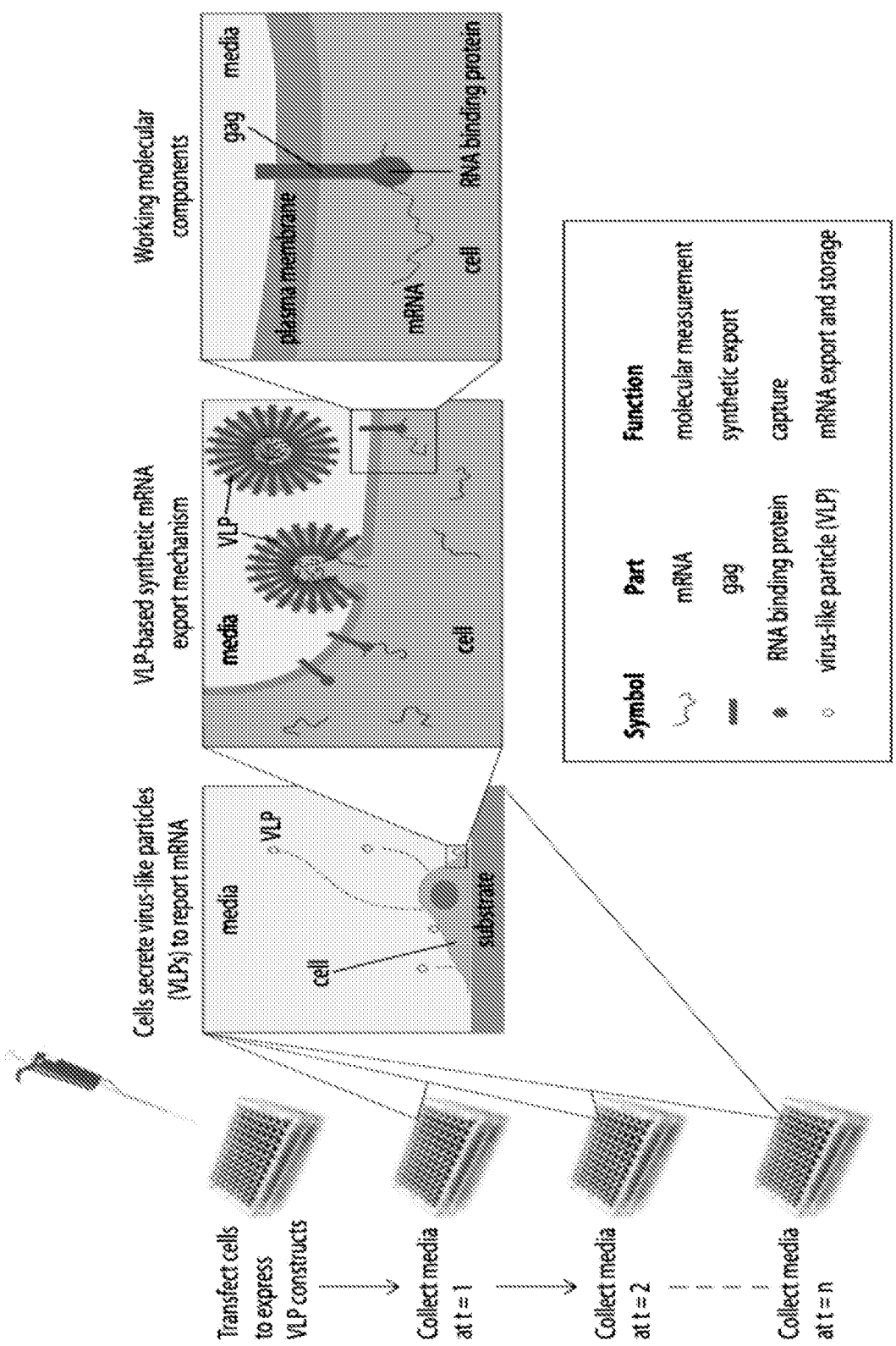
FIG. 1 is a diagram depicting a method for continuous monitoring of live cells, in accordance with certain example embodiments.
Figure 2:
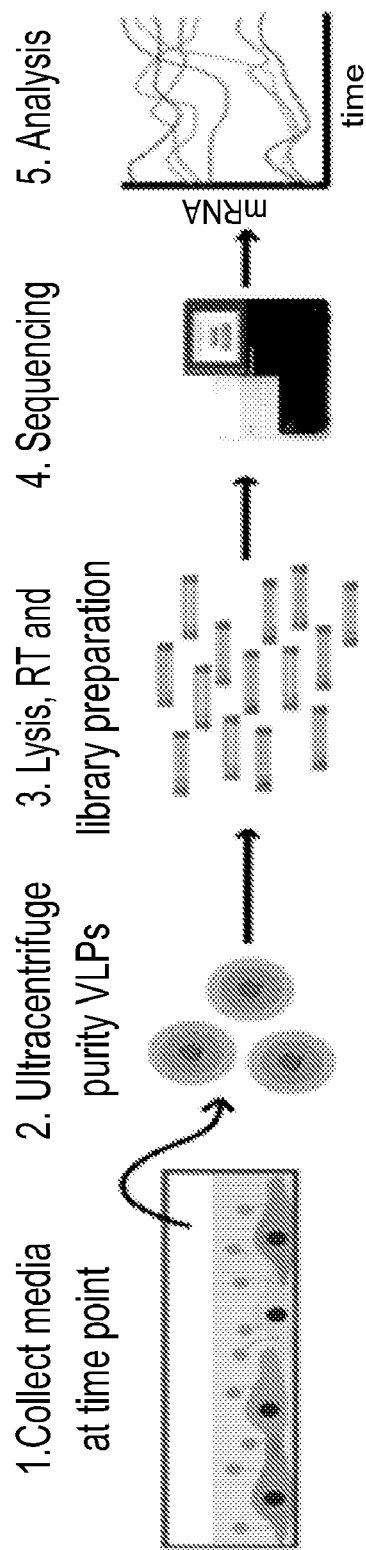
FIG. 2 is a diagram depicting a method for continuous gene expression analysis of live cells, in accordance with certain example embodiments.
Figure 3:
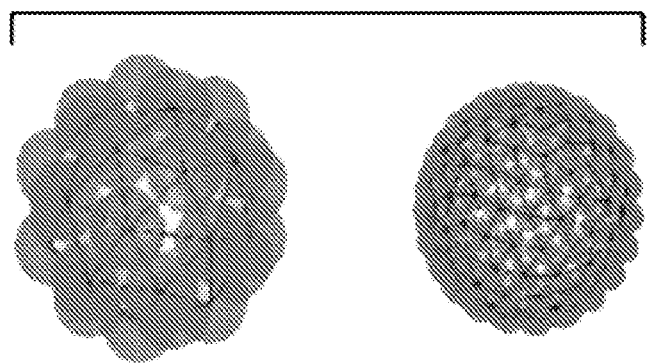
FIG. 3 is a diagram summarizing simulation of export compartment size and the theoretical number of mRNA that could be packaged inside an example export compartment.

Embodiments disclosed herein provide nucleic acid constructs and methods of use thereof that induce a live cell to give off sub-samples of the cell's cytosolic content. The term "cell" as used herein may be any cell type. In certain example embodiments, the cells are mammalian cells. The sampling can be general or can be targeted to a particular class of molecules or to specific types of molecules. The constructs facilitate generation of a read-out for high-throughput screens by combining engineered export with simple bulk sample and sample processing. Live cell sampling enables time course measurements and expands, for example, the applicability of transcriptional profiles obtained by single cell gene expression analysis. However, the constructs disclosed herein are not limited to transcriptional profiles, but may be used to sample any class of molecule whose export can be induced by expression of the constructs described herein. For example, the constructs may be used for sampling of small molecules, carbohydrates, lipids, nucleic acids, and proteins. The constructs may further comprise steric linkers, inducible promoters, and affinity domains, and enrichment or affinity tags as discussed in further detail below. Accordingly, when introduced into cells the constructs disclosed herein enable live cell sampling of cellular contents while maintaining cell viability. Cellular contents include nuclear as well as cytosolic contents.

Cell Sub-Sampling Export Constructs

In one aspect, the nucleic acid construct encodes a secretion-inducing protein. A secretion-inducing protein is a protein that when expressed induces a cell to export cellular contents in association with the secretion-inducing protein. Such constructs allow for the generalized sampling of cellular contents as the sample of cellular contents will be randomly dictated by the location within the cell that association with the secretion-inducing protein takes place. As used herein, and in the context of proteins encoded by the nucleic acid constructs described herein, a "protein" may refer to the full length sequence of the protein or only that portion of that protein that is necessary for the function for which the full length protein is otherwise expressed. In certain example embodiments, the nucleic acid construct may further comprise a nucleic acid encoding a localization signal to localize the secretion-inducing protein to a specific cell location such as the nucleus, mitochondria, endoplasmic reticulum, peroxisomes, and plasma membrane.

In certain example embodiments, the secretion-inducing protein is an export compartment protein. An export compartment protein may be any protein that self-assembles upon expression in a cell into an export compartment. In certain example embodiments, an export compartment is a spherical macromolecular assembly comprising a protein inner layer with or without an outer lipid containing membrane, with at least the export-compartment protein forming the inner protein layer. In certain example embodiments, the export compartment protein may only form a partial export compartment while retaining the ability to associate with and export the targeted cellular contents. In certain example embodiments, the export compartment protein is a viral export compartment protein that forms virus-like particles. Regarding embodiments that use viral export compartment proteins, the terms export compartment and virus-like particle (VLP) may be used interchangeably. Example viral export compartment proteins may include viral capsid proteins. In certain example embodiments, the viral capsid protein is a viral Gag protein. In certain example embodiments, the viral Gag protein is a lentivirus Gag protein. In certain example embodiments, the export compartment protein is encoded by the nucleic acid sequence of SEQ ID NO: 1.

Fusion Protein Constructs

In another aspect, the nucleic acid constructs comprise a nucleic acid sequence encoding a secretion-inducing protein domain and an affinity domain. The secretion-inducing domain may comprise the secretion-inducing proteins as described above. As opposed to the generalized sampling provided by the constructs described above, the construct expressing an affinity domain allows for more targeted sampling. The targeted sampling may be directed to a particular class of molecules or a particular subtype of molecules. For example, the affinity domain may bind all RNA molecules, or it may only selectively bind mRNA or microRNA molecules. Alternatively the targeted sampling may be directed to specific target molecules. The level of specificity is modulated by the selection of an appropriate affinity domain. The affinity domain comprises a protein or peptide with the ability to specifically bind the target cellular molecule.

The affinity domain may bind directly to a target molecule or may bind indirectly. For example, the affinity domain may bind to another molecule which is specific to the target molecule, such as but not limited to an antibody or an aptamer. In certain example embodiments, the affinity domain may comprise an immunoglobulin binding protein or peptide, such as Protein A or G. In certain other example embodiments, the affinity domain may comprise a nucleic acid binding protein that binds to a capture motif on a nucleic acid, such as an aptamer designed to bind the target molecule of interest. The antibody or aptamer may specifically target cellular nucleic acids, proteins, lipids, or carbohydrates, and may be delivered to the cells separately from the constructs disclosed herein.

In certain example embodiments, the affinity domain comprises a protein or peptide that binds small molecules. Example proteins or peptides that bind small molecules include, but are not limited to, albumins, globulins, or a peptide comprising a small-molecule binding site. Example albumins include bovine serum albumin (BSA), human serum albumin (HSA), and ovalbumin. Example globulins include $\alpha_1$-antitrypsin, $\alpha_1$-antichymotrypsin, orosomucoid, serum amyloid A, alpha 1-lipoprotein, haptoglobin, alpha-2u globulin, $\alpha_2$-macroglobulin, ceruloplasmin, thyroxine-binding globulin, $\alpha_2$-antiplasmin, protein C, $\alpha_2$-lipoprotein, angiotensinogen, $\beta_2$-microglobulin, plasminogen, angiostatins, properdin, sex hormone-binding globulin, and transferrin. Peptides comprising a small-molecule binding site allow for specific targeting of specific small molecules. Accordingly, the targeted small molecule and its known peptide binding site will dictate the composition of the affinity domain in such embodiments.

In certain example embodiments, the affinity domain may comprise a protein or peptide that binds cellular carbohydrates. Example proteins or peptides that bind cellular carbohydrates include lectins or proteins that form glycoprotein complexes. Example lectins include calnexin, calcireticulin, calmegin, L-type lectins such as ERGIC-53, VIP-36, and plant lectins, P-type lectins, such as mannose-6-phosphate receptors, C-type lectins, such as selectins, collectins, galectins, I-type lectins, R-type lectins, hyaluronan-binding proteins, ficolins, pentraxins, beta3-integrins, annexins, amphoterin, and complement factor H. Example glycoproteins include typical glycoproteins, such as alkaline phosphatase, 3-N-acetyl D-hexosaminidase, carboxypeptidase, snake venom toxins, toad toxins, chorionic gonadotropin, FSH, TSH, LH, glycophorin, rhodopsin, avidin, fibronectin ceruloplasmin, transferrin; glycosaminoglycans, such as, hyaluronate, heparin, proteochondroitin sulfate, kerato sulfate, and chondroitin sulfate; and collagens.

In certain example embodiments, the affinity domain may comprise a protein or peptide that binds cellular lipids. Example proteins or peptides that bind cellular lips include apolipoproteins, scavenger receptors, and fatty acid binding proteins (FABP).

In certain example embodiments, the affinity domain may comprise a protein or peptide that binds another cellular protein or peptide. For example, affinity domain may comprise a protein or peptide that is the substrate for a cellular peptide. Peptides comprising a peptide or protein binding site allow for specific targeting of specific cellular proteins or peptides. Accordingly, the targeted protein and its known peptide binding site will dictate the composition of the affinity domain in such embodiments. Alternatively, the affinity domain may comprise a general protein binding molecule such an albumin.

In certain example embodiments, the affinity domain may comprise a protein or peptide that binds cellular RNA. The protein or peptide may bind single stranded or double stranded RNA. The protein or peptide may bind ribosomal RNA, transfer RNA, mRNA, non-coding RNA, or microRNAs. The protein or peptide may include a RNA-recognition domain, a K-homology domain (Type I or II), a double-stranded RNA-binding domain, a zinc finger-CCHH domain, a zinc finger-CCCH domain, a Si domain, a PAZ domain, a PIWI domain, a TRAP domain, a Pumillo domain, or a SMA domain. In certain example embodiments, the affinity domain comprises a poly-A binding protein (PABP) for binding mRNA. In certain other example embodiments, the affinity domain comprises an Argonaute protein for binding microRNAs. In certain example embodiments, the affinity domain comprises a protein encoded by the nucleic acid sequence of SEQ ID NO: 2 or SEQ ID NO: 3.

General Construct Elements

In certain example embodiments, all of the constructs disclosed herein may further include an inducible promoter to control expression of the construct elements. Inducible promoters may include any suitable inducible promoter system. As recognized by one of ordinary skill in the art, the suitability of a particular inducible promoter system is dictated by the cellular system in which the constructs will be used. Accordingly, the biotic or abiotic factors that induce the activity of such promoters must be compatible with the cellular system in which the constructs of the present invention will be used. For example, a biotic or abiotic factor that negatively impacts cell viability or significantly alters gene expression of the cell in the context of the biological condition being studied would not be a suitable inducible promoter system. The inducible promoter may be a suitable chemically-regulated promoter or suitable physically-regulated promoter. The chemically-regulated promoter may be a suitable alcohol-regulated promoter, tetracycline-regulated promoter, steroid-regulated promoter, or a metal-regulated promoter. The physically-regulated promoters may be a temperature-regulated promoter or a light-regulated promoter. In certain example embodiments, the inducible promoter is a tetracycline-regulated promoter such as pTet-On, pTet-Off, or pTRE-Tight. In one example embodiment, the promoter is a Dox-inducible promoter. In certain example embodiments, the promoter may be a tissue-specific promoter. Example tissue-specific promoters include, but are not limited to, a neuron-specific enolase promoter, a tubulin α1 promoter, a glial-fibrillary acid protein promoter, a myosin light chain-2 promoter, a preprodndothelin-1 promoter, a tie promoter, a SM22α promoter, a α1-AT promoter, an albumin promoter, a side-chain-cleavage enzyme promoter, or a kidney-androgen responsive protein protein.

In certain example embodiments, all of the constructs disclosed herein may further comprise a steric linker sequence. The encoded steric linker sequence may be a random peptide sequence of a particular size. The size of the steric linker sequence may control the rate of export, the size of the export compartment or both. For example, a larger linker sequence appended to an export compartment protein may slow the rate at which the export compartment proteins can self-assemble by creating steric hindrance that slows the rate of assembly. Likewise, a larger linker sequence that must be incorporated into the export compartment may increase the size of the export compartment formed. In certain example embodiments, the steric linker is approximately 2 to approximately 12 amino acids in size. In certain example embodiments, the linker sequence is located on the N-terminus of the secretion-inducing protein. In certain other example embodiments, the linker sequence is located on the C-terminus of the secretion-inducing protein.

In certain example embodiments, all of the constructs disclosed herein may further comprise an enrichment tag or affinity tag. Enrichment tags include, but are not limited to Flag, CBP, GST, HA, HBH, MBP, Myc, polyHis, S-tag, SUMO, TAP, TRX and V5. Enrichment tags can also include engineered transmembrane domains, in order to increase the likelihood of surface presentation. Capture methods include, but are not limited to magnetic beads, columns and centrifugation. Enrichment tags may be used to facilitate collection and enrichment of expressed VLPs using a corresponding affinity-based method.

In certain example embodiments, all of the constructs may further include a construct self-reporter, such as RFP, YFP, GFP, or any other marker molecule that can be expressed and detected in a cell. The self-report marker or protein may be connected to the rest of the construct by a cleavable linker, such as a p2A linker to allow release of the self-reporter molecule after detection and prior to export compartment formation. The self-reporter can be used to confirm to confirm successful delivery of the construct to targeted cells or tissues.

Vectors

In another aspect, the embodiments disclosed herein are directed to vectors for delivering the constructs disclosed herein to cells. In certain example embodiments the vector is a viral vector. Suitable viral vectors include, but are not limited to, retroviruses, lentiviruses, adenoviruses and AAV. In certain other example embodiments, the vector is a non-viral vector. Suitable non-viral vectors include, but are not limited to, cyclodextrin, liposomes, nanoparticies, calcium chloride, dendrimers, and polymers including hut not limited to DEAE-dextran and polyethylenimine. Further non-viral delivery methods include electroporation, cell squeezing, sonoporation, optical transfection, protoplast fusion, impalefection, hydrodynamic delivery and magnetofection. For non-viral vectors, delivery to a microbe may be facilitated by standard transfection technologies such as electric pulsing, electroporation, osmotic shock, and polymeric-based delivery systems.

Methods of Live Cell Sampling

In one example embodiment, a method for continuous monitoring of live cells comprises delivering a nucleic acid construct encoding a secretion-inducing protein to one or more cells. When expressed, the secretion-inducing protein induces export of cellular contents in association with the secretion-inducing protein. In certain example embodiments, the secretion-inducing protein is a protein that self-assembles to form an export compartment. In the process of self-assembling to form the export compartment, cellular contents are randomly packaged within the export compartment. The export compartment is then exported from the cell. For example, the export compartment may be released into the cell culture media. The media may then be collected and the sample isolated. For example, the export compartments may be isolated from the cell culture media by ultracentrifugation, or other methods that separate components based on size or density. The isolated export compartments may then be lysed and the cellular contents analyzed. Isolated export compartments may be collected over multiple time points from the same cells or population of cells. This approach provides a generalized sampling of cellular contents and may be used to track changes in cellular contents over time. As noted above, the constructs may further include an inducible promoter to control at what time points the expression of the export compartment is turned on and off.

In certain example embodiment, the constructs are delivered to cells in a viral vector. In certain other example embodiments, the constructs are delivered to cells in non-viral vectors. Suitable viral vectors include, but are not limited to, retroviruses, lentiviruses, adenoviruses and AAV. In certain other example embodiments, the vector is a non-viral vector. For non-viral vectors, delivery to a microbe may be facilitated by standard transfection technologies such as electric pulsing, electroporation, osmotic shock, and polymeric-based delivery systems.

In another example embodiment, a method for continuous monitoring of live cells comprises delivering a nucleic acid construct encoding a fusion protein comprising an secretion-inducing domain and an affinity domain. The secretion-inducing protein drives induces export as described above, the affinity domain comprises a protein or peptide selectively binds a target class of cellular molecules for export from the cell. For example, it may be desirable to track changes in the profile of small molecules (or small molecule metabolites), lipids, carbohydrates, proteins, or nucleic acids over time. As discussed above, certain affinity proteins can be selected for binding these classes of molecules. In certain example embodiments, the secretion-inducing protein is an export compartment protein disclosed herein, that when expressed, self-assembles to form an export compartment as described herein. In the process of self-assembling to form the export compartment the affinity domain binds to the target class of cellular molecules resulting in the packaging of the target class of cellular molecules with the export compartment. The export compartment containing the target cellular molecule is then exported from the cell. For example, the export compartment may be released into the cell culture media. The media may then be collected and the sample isolated. For example, the export compartments may be isolated from the cell culture media by ultracentrifugation, or other methods that separate components based on size or density. The isolated export compartments may then be lysed and the cellular contents analyzed. Isolated export compartments may be collected over multiple time points from the same cells or population of cells. As noted above, the constructs may further include an inducible promoter to control at what time points the expression of the export compartment is turned on and off.

In certain example embodiments, the method involves the use of a fusion protein comprising a Gag protein and a PABP protein to allow for live sampling of mRNAs produced by the cells over time. The method may further comprise identifying the isolated mRNAs by sequencing the isolated mRNAs.

In certain example embodiment, the constructs are delivered to cells in a viral vector. In certain other example embodiments, the constructs are delivered to cells in non-viral vectors. For non-viral vectors, delivery to a microbe may be facilitated by standard transfection technologies such as electric pulsing, electroporation, osmotic shock, and polymeric-based delivery systems.

The invention is further defined with reference to the following numbered clauses:

1. A nucleic acid construct comprising a nucleic acid sequence encoding a secretion-inducing protein that induces live cells to export cellular contents when expressed in a cell.
2. The nucleic acid construct of clause 1, further comprising an inducible promoter to control expression of the secretion-inducing protein.
3. The nucleic acid construct of clause 1, wherein the secretion-inducing protein self-assembles upon expression to form an export compartment.
4. The nucleic acid construct of clause 3, further comprising a linker sequence of a particular size, the size of the linker sequence controlling a rate of export, a size of the export compartment, or both.
5. The nucleic acid construct of clause 1, wherein the secretion-inducing protein is a viral capsid protein.
6. The nucleic acid construct of clause 5, wherein the viral capsid protein is a Gag protein.
7. The nucleic acid construct of clause 6, wherein the Gag protein is a lentivirus Gag protein.
8. The nucleic acid construct of clause 1, wherein the nucleic acid sequence encoding secretion-inducing protein is encoded by SEQ ID NO: 1.
9. A nucleic acid construct comprising a nucleic acid sequence encoding a fusion protein, the fusion protein comprising a secretion-inducing domain and an affinity domain.
10. The nucleic acid construct of clause 9, further comprising an inducible promoter to control expression of the nucleic acid sequence encoding the fusion protein.
11. The nucleic acid construct of clause 9, wherein the secretion-inducing domain self-assembles upon expression to form an export compartment.
12. The nucleic acid construct of clause 10, wherein the secretion-inducing protein is a viral capsid protein.
13. The nucleic acid construct of clause 11, wherein the viral capsid protein is a Gag protein.
14. The nucleic acid construct of clause 12, wherein the Gag protein is a lentivirus Gag protein.
15. The nucleic acid construct of clause 9, wherein the affinity domain binds small molecules, carbohydrates, lipids, proteins, or nucleic acids.
16. The nucleic acid construct of clause 9, wherein the affinity domain is an albumin, a lipoprotein, a globulin, or peptide comprising a small-molecule binding site.
17. The nucleic acid construct of clause 9, wherein the affinity domain is lectin, or a peptide that binds a carbohydrate specific antibody, carbohydrate specific antibody fragment, or a carbohydrate specific aptamer.

18. The nucleic acid construct of clause 9, wherein the affinity element is an apolipoprotein, scavenger receptors, fatty acid binding proteins (FABP), or a peptide that binds a carbohydrate specific antibody, carbohydrate specific antibody fragment, or a carbohydrate specific aptamer.

19. The nucleic acid construct of clause 9, wherein the affinity element is a protein-specific antibody, a protein-specific antibody fragment, or a peptide that binds protein-specific aptamer.

20. The nucleic acid construct of clause 9, wherein the affinity element is a peptide comprising a DNA-binding domain, a RNA-binding domain, an Argonaute protein or a poly-A binding protein (PABP).

21. The nucleic acid construct of any one of clauses 1 to 20, wherein the secretion-inducing protein self-assembles to form an export compartment approximately 10 nm to approximately 500 nm in diameter.

22. A vector comprising the nucleic acid construct of any one of clauses 1 to 21.

23. The vector of clause 22, wherein the vector is a non-viral vector.

24. The vector of clause 22, wherein the vector is a viral vector.

25. A kit comprising the nucleic acid construct of any one of clauses 1 to 21.

26. A kit comprising the vectors of any one of clauses 22 to 24.

27. A method for continuous monitoring of live cells comprising:
delivering into one or more cells a nucleic acid construct encoding a secretion-inducing protein;
expressing the nucleic acid construct in the one or more cells, wherein expression of the secretion-inducing protein in the one or more cells results in the export of cellular contents in association with the secretion-inducing protein; and
isolating the exported cellular cytosolic contents at one or more time points.

28. The method of clause 27, wherein the nucleic acid construct is the nucleic acid construct of any one of clauses 1 to 8.

29. The method of clause 27, wherein the nucleic acid construct is delivered using a non-viral or viral vector.

30. The method of clause 27, wherein the nucleic acid construct is a nucleic acid construct of any one of clauses 9 to 20.

31. The method of clause 30, further comprising isolating the exported small molecules, carbohydrates, lipids, proteins, or nucleic acids.

32. The method of clause 30, wherein the affinity element is a poly-A-binding protein (PABP) that binds mRNA in the cell.

33. The method of clause 30, further comprising sequencing the isolated mRNA exported from the cell.

This invention is further illustrated by the following examples, which are not to be construed in any way as imposing limitations upon the scope thereof.

EXAMPLES

Example 1

Mammalian cells turn over approximately 14% of the transcriptome per hour on average (Yang E, Genome Research 2003), and simulations (described below) show that mRNA can theoretically be exported in VLPs at 100% of the cell's normal synthesis rate. By sampling at 25% of the turnover rate, 3% of the total transcriptome could be sampled per hour, or 500-15,000 transcript molecules per hour. By fine-tuning the transcriptional and translational dynamics of export compartment production, cellular RNA should be sampled at a specified rate of 0.1% to 3% of the normal synthesis rate. Even with estimated sample preparation methods that are approximately 50% efficient, detection of 250-7500 collected transcript molecules per cell per hour can be achieved. This 'integration time' can be varied to resolve the necessary timescales associated a particular question. A tunable trade-off exists between temporal resolution and the degree of perturbation to the cell.

Packing of 28-150 transcripts per VLP inner surface is estimated. This estimate is derived from a range in VLP radius of 80-130 nm and an mRNA radius of gyration of 16.8-20.8 nm (mRNA radius of gyration from Gopal A, RNA 2012). With these numbers in mind, it is possible to calculate that the burden of VLP production necessary to collect 15,000 transcript molecules per hour corresponds to as little as 0.01% of the cell's total protein (total protein per cell count from Siwiak M, PLoS ONE 2013).

To export mRNA in a minimally-biased manner for genome-wide expression profiling, a Gag-PABP fusion was constructed and export tested from HEK293 cells. The construct is safe and replication-deficient, as it contains neither reverse transcriptase nor integrase. See FIG. 1. Poly(A)-binding protein (PABP), which binds to the poly(A) tail of mRNA, will be used as an mRNA binding domain for synthetic mRNA export machinery. The PABP domain will recruit mature transcripts from the cytoplasm, while the Gag domain will allow for export of captured mRNA through membrane budding and VLP formation. The overall rate of export can be optimized for the desired sampling frequency and cell type by controlling the Gag-PABP fusion expression level.

Figure 4:
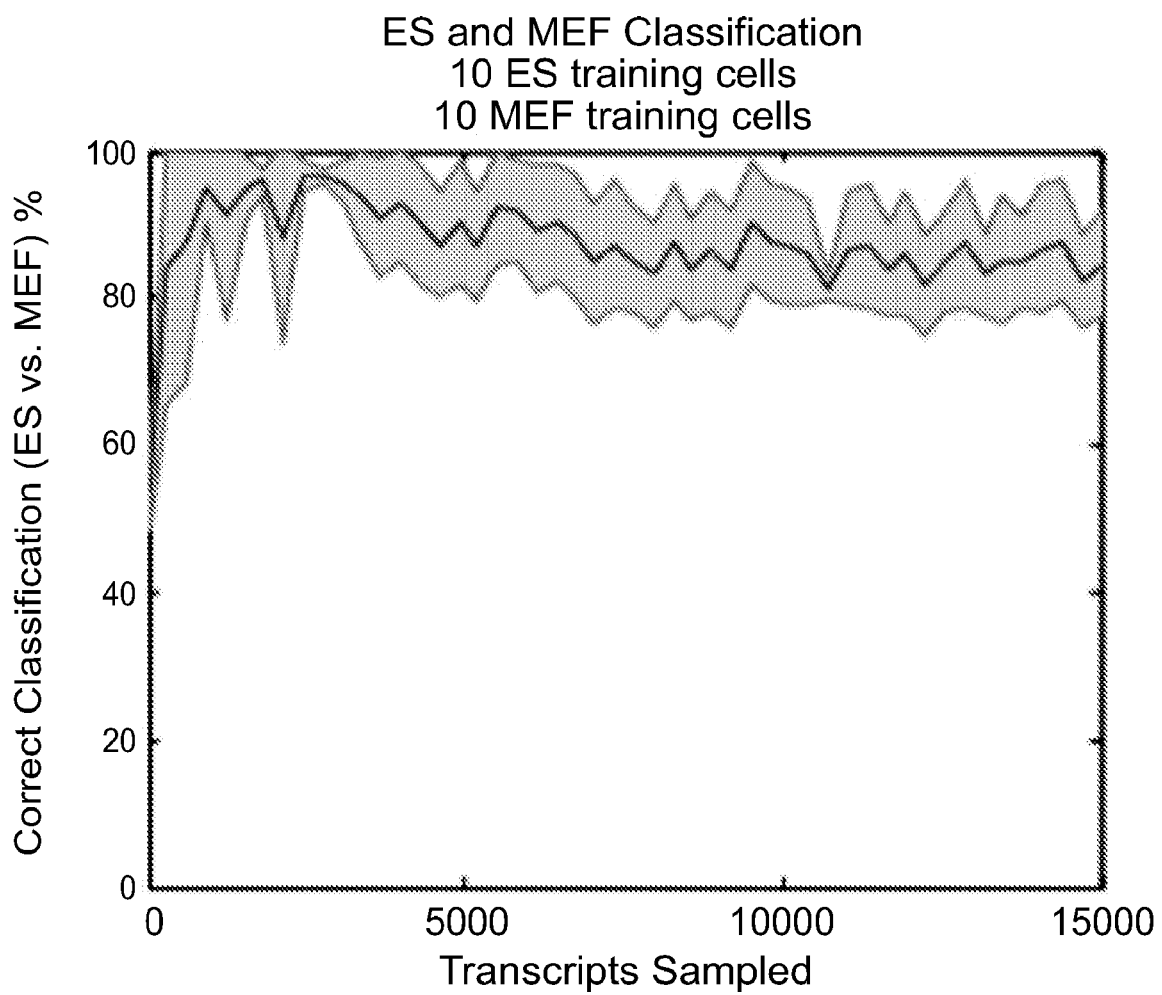
FIG. 4 is a graph showing a simulation based on exclusive reads per cell type that allows for >80% accuracy of prediction with a simple algorithm that uses inner-products and training on 10 cells per cell type.
Figure 5:
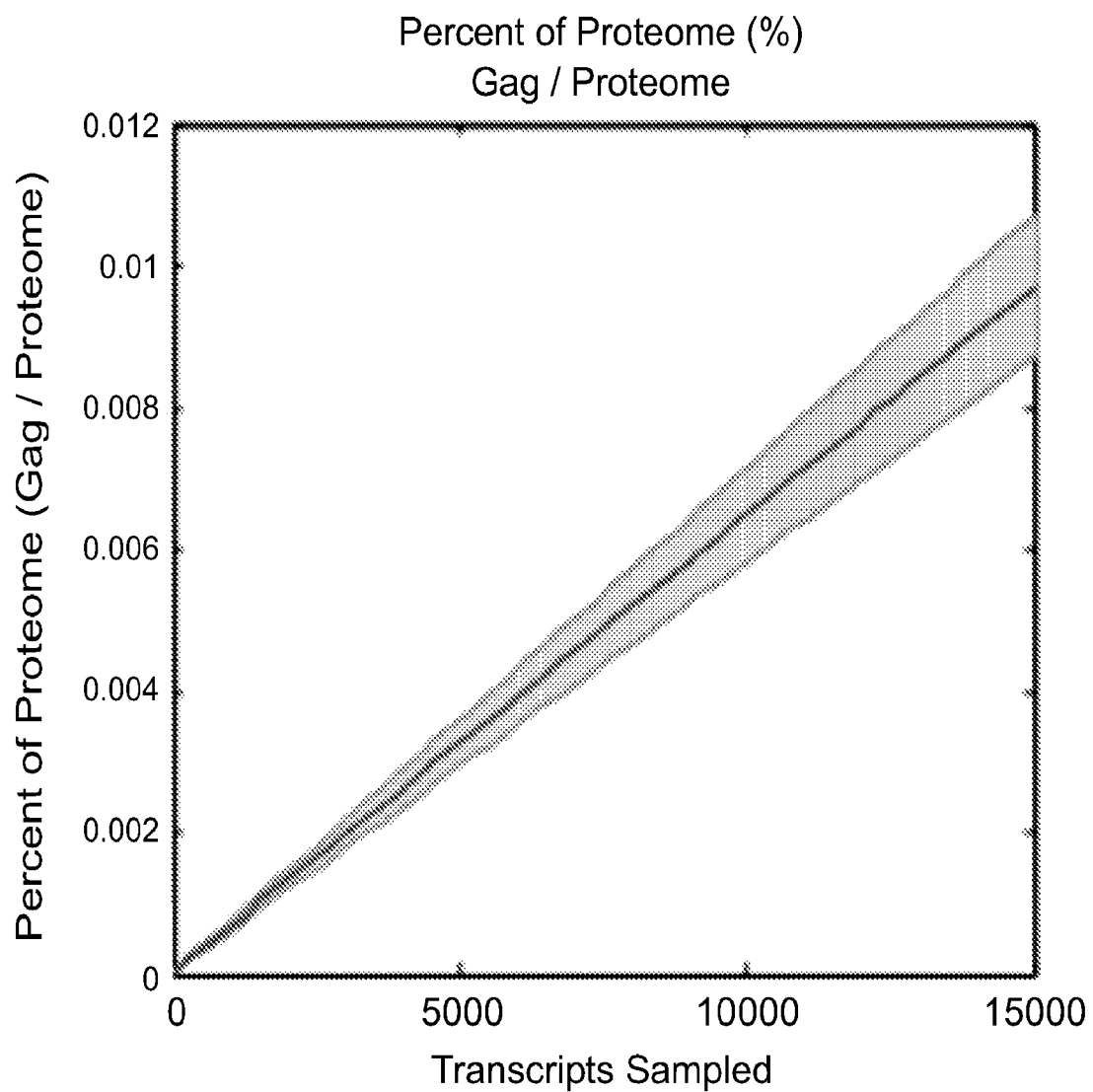
FIG. 5 is a graph showing the percent of the proteome that is composed of Gag proteins per number of transcripts sampled.
Figure 6:
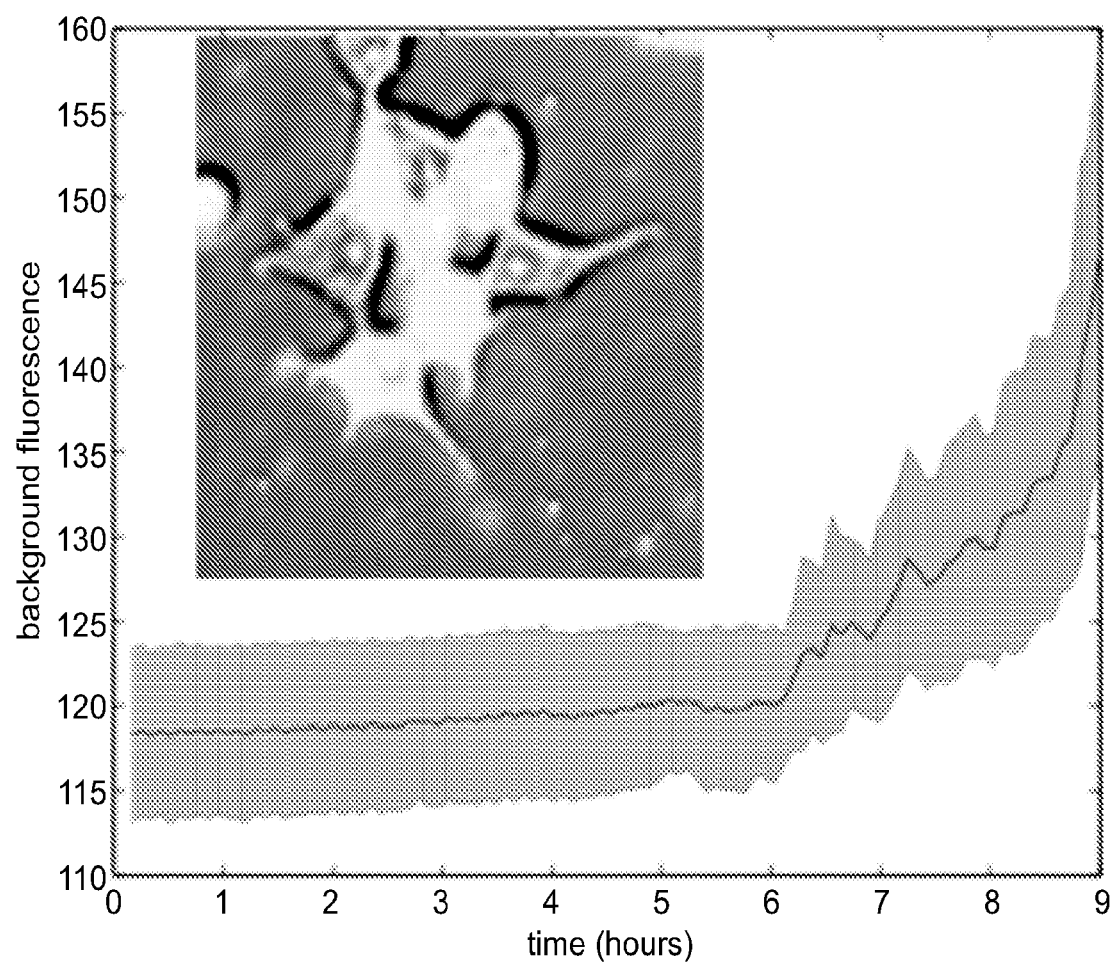
FIG. 6 is a graph with picture insert showing formation and export of export compartments from HEK293 cells by expression of a Gag-YFP construct. Small fluorescent particles appear in the media over time, and the total fluorescence of the media from the export compartments is observed to increase over time. The error bands in the graph represent +/−SD.
Figure 7:
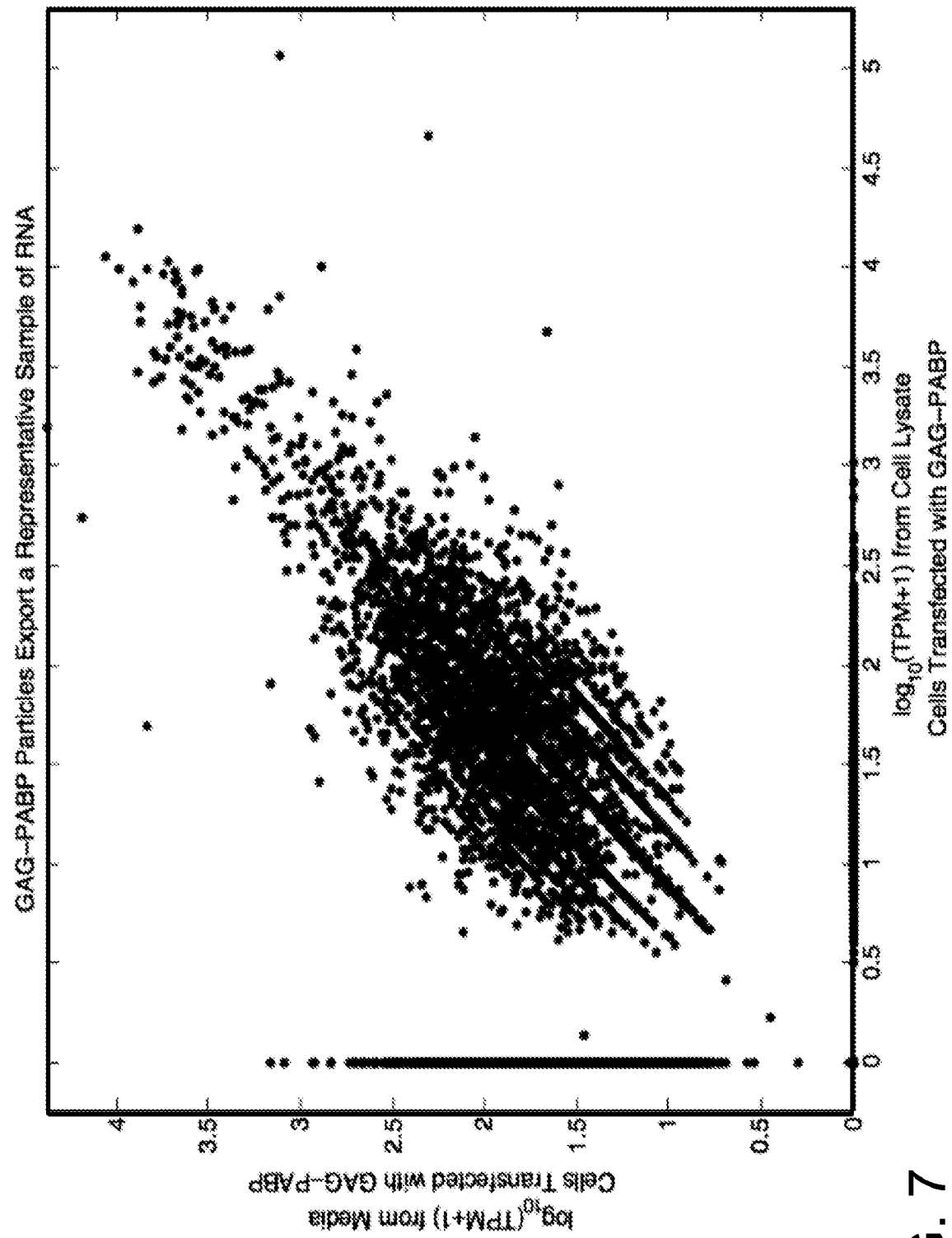
FIG. 7 is a graph depicting Gag-PABP induced export for a representative sample of RNA using nucleic acid constructs in accordance with certain example embodiments. Transcripts per million (TPM) scores for different genes were plotted against each other. Log-transformed TPM scores from the lysate of cells transfected with Gag-PABP agreed with TPM scores from the lysate of purified export compartments (VLPs) from cells transfected with GAG-PABP. The cells used in the study were HEK293 cells.
Figure 8:
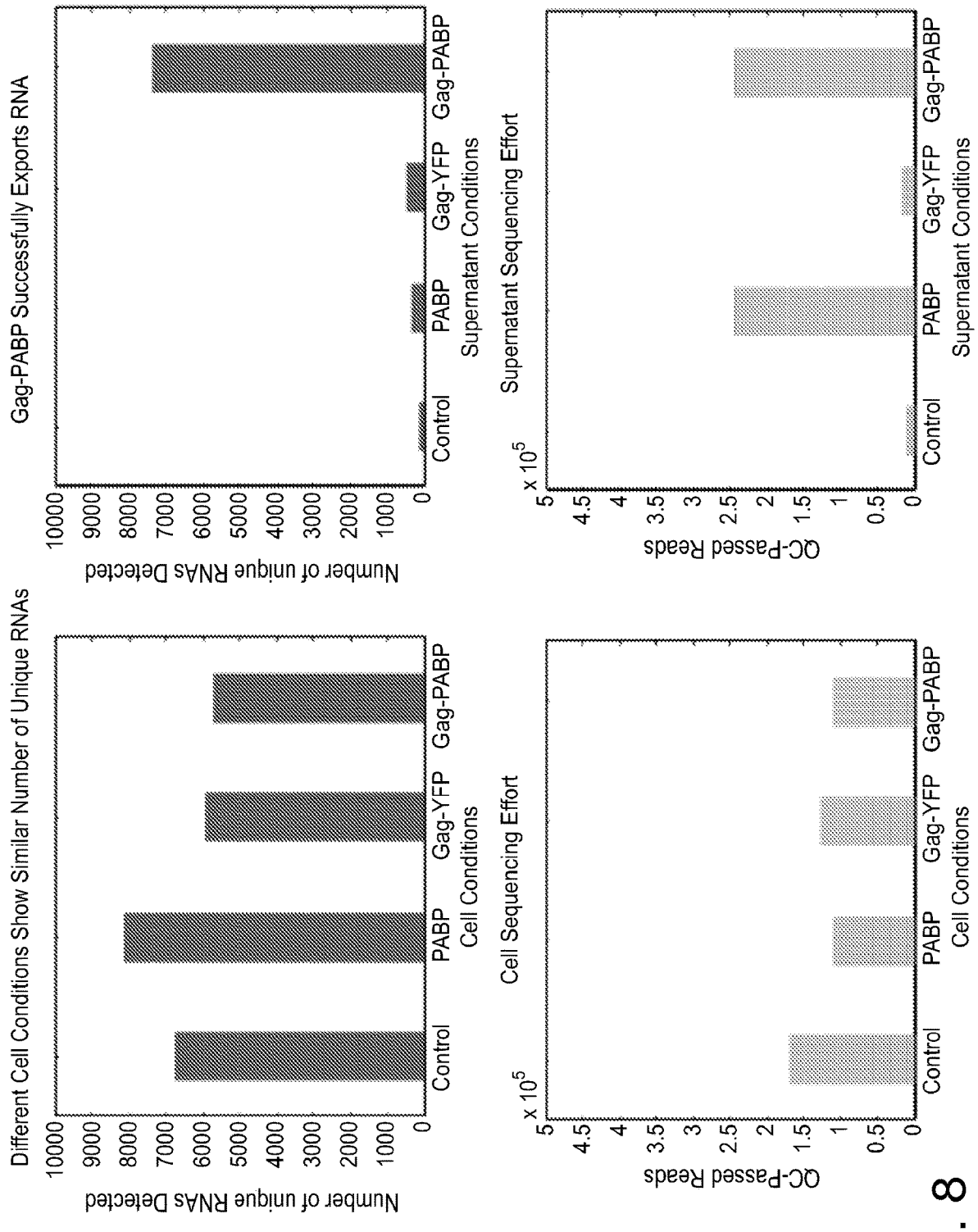
FIG. 8 is a set of graphs (A-D) demonstrating that Gag-PABP fusion proteins, in accordance with certain example embodiments, successfully export RNA and can be collected in media. RNAseq libraries were made via the Smartseq2 protocol, and the number of unique RNAs was determined from different conditions of HEK293 cells (A). Cells transfected with different constructs (PABP, Gag-YFP, and Gag-PABP) were lysed, and the number of unique RNAs was determined for each sample. The lysates showed comparable complexity across conditions (A). Media was collected from the cell conditions shown in (A), and export compartment (VLP) purification was carried out by standard methods. RNA complexity was shown to be minimal and not comparable to cell lysates and for the control (no plasmid delivery), PABP and Gag-YFP. However, Gag-PABP showed a complexity that matched that of cell lysates, suggesting that RNA was indeed exported (B). QC-passed reads for cell lysate conditions (C). QC-passed reads for supernatant conditions (D).
Figure 9:
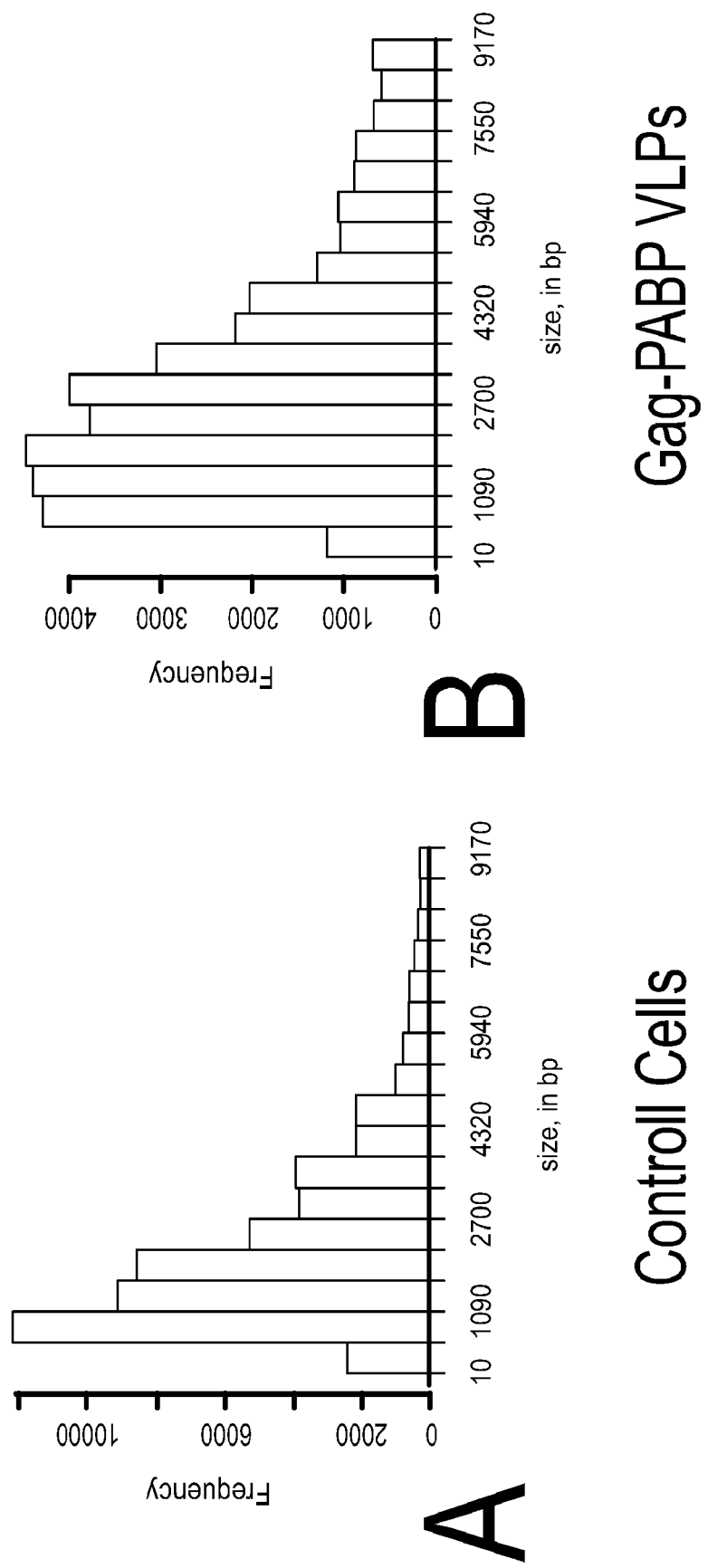
FIG. 9 is a set of graphs (A-B) demonstrating that large RNAs are not excluded from export compartments (VLPs). The RNA size distribution derived from HEK293 cell lysates is shown on the left (A). The RNA size distribution from VLPs expressed in HEK293 cells is shown on the right (B). Comparison of the two graphs demonstrates that large RNAs are not excluded from the export compartments. The distribution shift towards larger RNAs in VLPs can be explained by volume exclusion.
Figure 10:
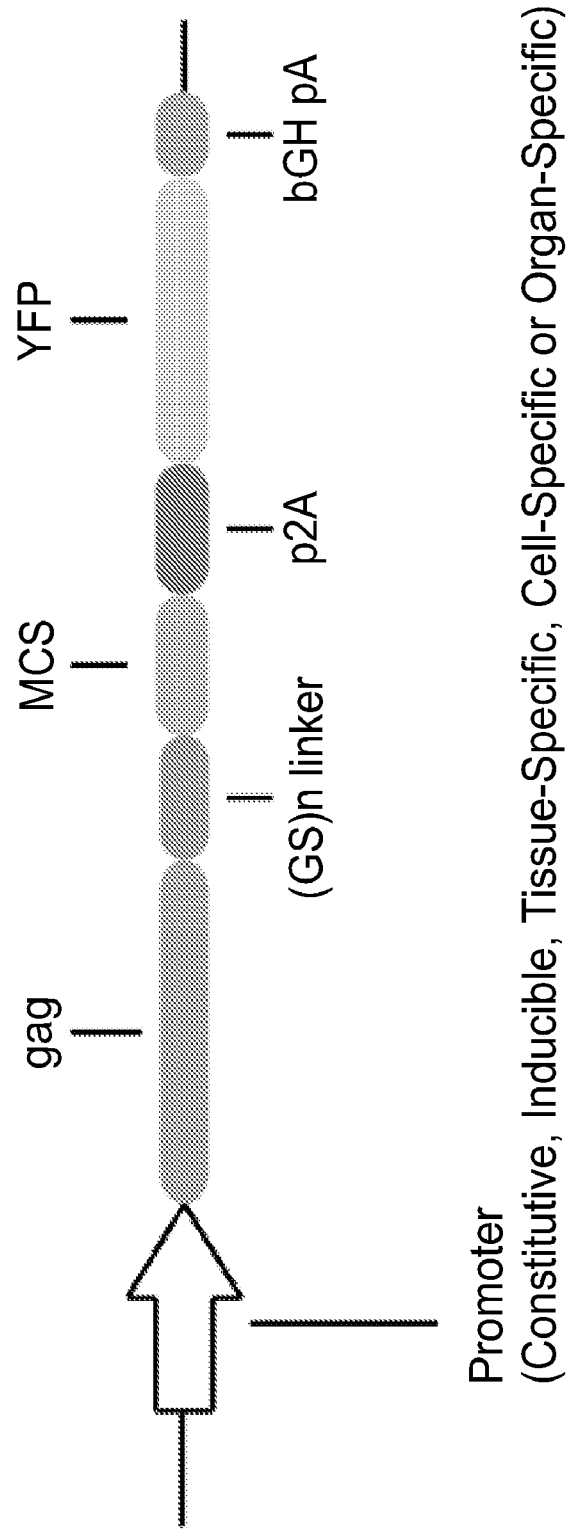
FIG. 10 is a diagram of a DNA construct in accordance with certain example embodiments. The diagram shows a possible DNA construct for making Gag fusion proteins. The glycine-serine (GS) linker functions as a flexible amino acid linker between the gag protein and the cloned protein of interest. The cloned protein of interest is ligated into the construct in the multiple cloning site (MCS) via standard restriction cloning techniques. The p2A linker serves as a self-cleaving linker, allowing yellow fluorescent protein (YFP) to be translated from the same transcript without fusion. In certain example embodiments, the p2A linker is SEQ ID NO: 4.
Figure 11:
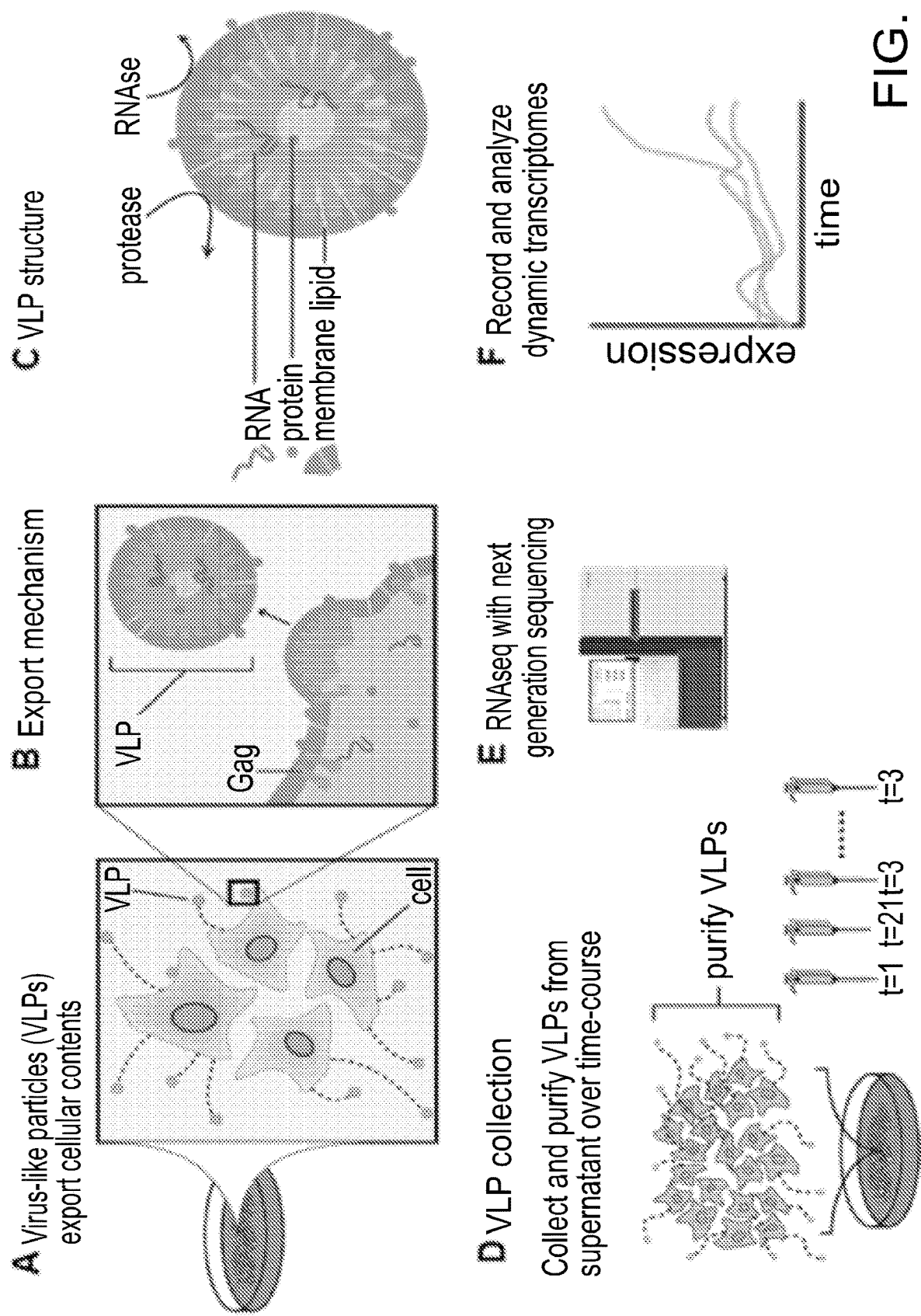
FIG. 11 is a schematic providing an overview of cellular self-reporting using VLPs. (A) Virus-like particles (VLPs) export cellular contents. (B) Export mechanism showing VLP formation and release. (C) VLP structure. (D) VLP collection from supernatant and downstream purification by filtration and ultracentrifugation techniques. (E) RNAseq is carried out on the RNA packaged within VLPs after the necessary library preparation. (F) Live-cell transcriptomes are recorded for further downstream analysis.
Figure 12:
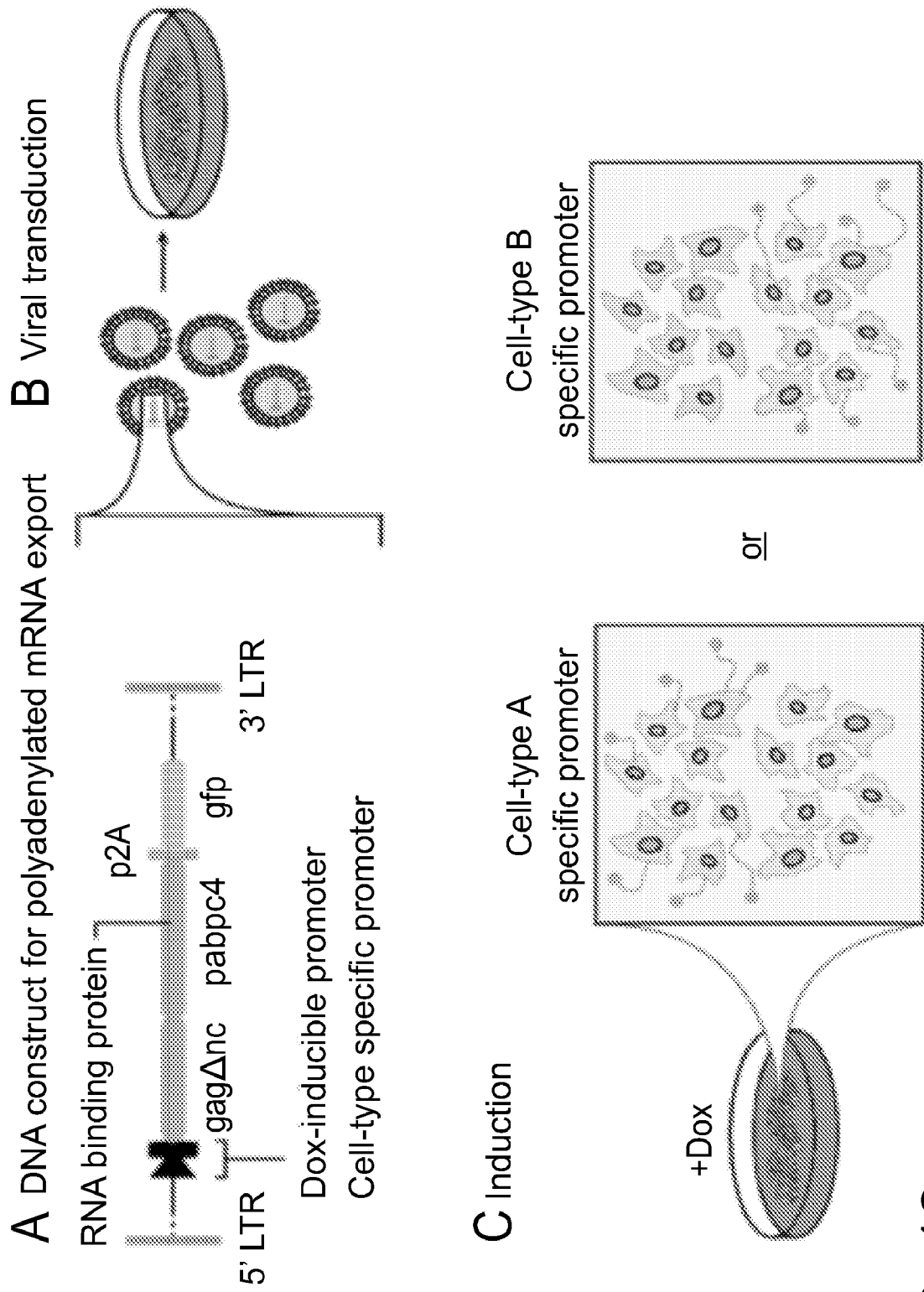
FIG. 12 is a schematic of an example genetically encodable self-reporting construct delivery and control. (A) The genetically encodable GagΔNC-PABPC4 construct for lentiviral delivery. The construct is engineered to have a p2A self-cleaving peptide for the translation of a labile GFP report. The overall construct can also be engineered to have a doxycycline-inducible promoter or a cell-type specific promoter. (B) Viral transduction can be done at low multiplicity of infection, and then selection can be conducted in order to ensure stable single-copy integrations of the construct. (C) Expression can be induced by titrating doxycycline, or by having a certain cell-state (belonging to a specified cell-type).

A rate of VLP export of mRNA can be determined by carrying out highly controlled VLP collection experiments with an inducible Gag-PABP fusion from a known number of cells. RNA from the VLPs will then be extracted and used to prepare RNA-Seq libraries (FIG. 4) with unique molecular identifiers and a spike-in control (ERCC from Life Technologies). By comparing the RNA-seq of bulk cell lysate of self-reporting cells to the lysate of normal cells, the transcriptional defect caused by the VLP export system can be detected. Similar analysis of the extracted VLPs compared to bulk controls can be used to estimate mRNA export per cell per unit time and any sampling biases (eg against large transcripts). These tests will be carried out over a range of different promoter strengths to find the optimal expression rate, for all cells of interest.

GFP+ self-reporting HEK293 cells will be plated in such a way that there is 1 cell per well of a 384 well plate on average. To remain certain that GFP+ cells are self-reporting, GFP and Gag-PABP will be delivered in the same vector. This experiment will allow the plate to be imaged to determine the number of GFP+ self-reporting cells, the media retrieved to collect VLPs. After collection, VLPs will be purified by standard virus purification protocols. VLP lysis will be carried out using standard lysis techniques, and Illumina-ready DNA libraries will be constructed using Smart-seq2 (Picelli S, Nature Protocols 2014). By indexing the media from each well separately through the Smart-seq2 protocol, the sequencing reads can be traced to the original wells to determine the accuracy of VLPs as reporter systems.

This will enable GFP expression as a function of time to be observed, and a correlation between GFP reads and cell fluorescence to be determined. The individual cells will be collected at the final time point and collected and prepared for RNA-Seq in the same plate.

Example 2—Gag-PABP Preparation and Characterization

Gibson assembly for Gag-PABP fusion proteins. Standard lipofectamine transfection protocol for HEK293 cells was used. Cells were transfected and supernatant/lysates were collected after 48 hours. VLPs were purified by filtering 3 mL of supernatant from cell culture (~1e6 cells) diluted to 10 mLs on a 0.45 µm PVDF filter. The 10 mL of filtrate was brought up to 20 mL and gently poured into ultracentrifuge conicals. Using a 5 mL serological pipette, 5 mL of 20% sucrose in 10×PBS (0.1M PBS) was added to the bottom of the conicals to create a sucrose gradient. The tubes were spun at 26k (RPM) for 3 hours at 4° C. The supernatant was removed and re-suspended in 100 µL of PBS and stored in −80° C.

Cell and VLP lysis was conducted using standard procedures in RLT lysis buffer.

Smartseq2 library construction was used to make Illumina-ready sequencing libraries. Sequencing was carried out on a MiSeq Illumina flow cell. See FIGS. 6-10 and Brief Description of Drawing Section regarding characterization of the Gag-PABP construct.

Example 3—In Vitro Export Data

Figure 13:
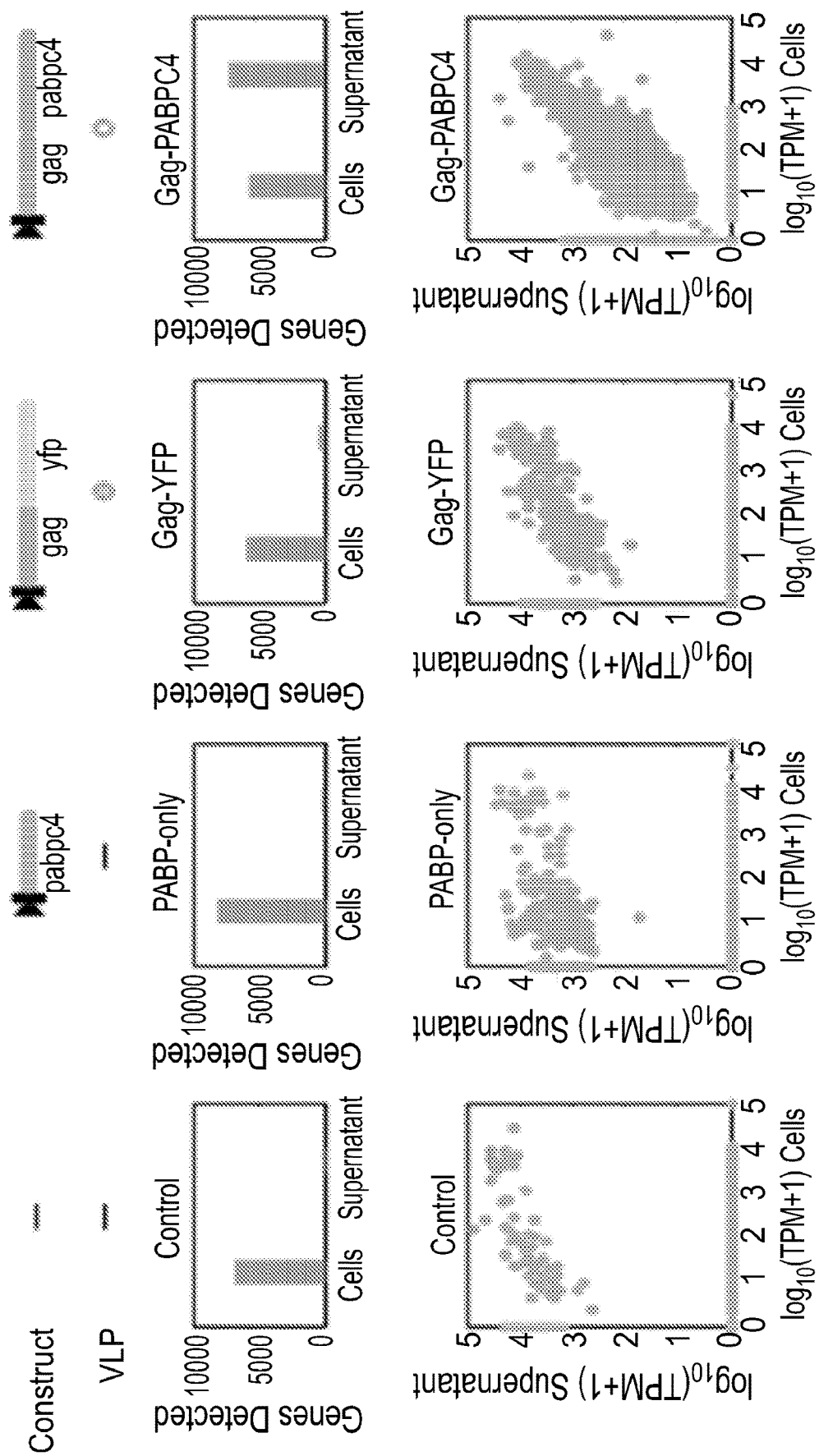
FIG. 13 provides a set of graphs showing in vitro RNAseq data demonstrating successful mRNA export from HEK293 cells.

FIG. 13 shows that Gag-PABPC4 successfully exports mRNA from HEK293 cells, as the number of genes detected from the VLPs is on the order of the number of genes detected from cell lysate. Further, the transcripts per million (TPM) align well for Gag-PABPC4 VLPs and their corresponding cell lysate, suggesting that mRNA exported by VLPs may be a representative subset of the transcriptome. The three controls were i) untransfected cells ii) PABPC4 only and iii) Gag-YFP. These controls showed minimal export, as the number of genes detected in the supernatant was several orders of magnitude lower than the number of genes detected in the cells. DNA constructs for export were made via Gibson assembly, and transient transfections of different constructs were carried out in order to examine feasibility. Transient transfections were conducted on HEK293 cells with lipofectamine, which was used per manufacturer's instructions. VLPs were collected from supernatant by first centrifuging the supernatant at 2000 ref for 10 minutes to pellet floating cells and debris. The pelleted cells and debris were stored for library prep. The resulting supernatant was then passed through a 0.22 um cellulose acetate filter, in order to exclude unpelleted cells and debris. The filtrate was then ultracentrifuged at 26k rpm for 3 hours with a sucrose cushion for VLP pelleting. The pelleted VLPs were resuspended in 1×PBS and were put through lysis and library prep according to the SMARTseq2 protocol. The stored cell pellet was put through the identical lysis and library prep protocol. RNAseq data suggested that the Gag-PABPC4 more effectively exported mRNA than Gag-YFP.

Example 5—Constructs from VLPs after Induction by DLS

Figure 14:
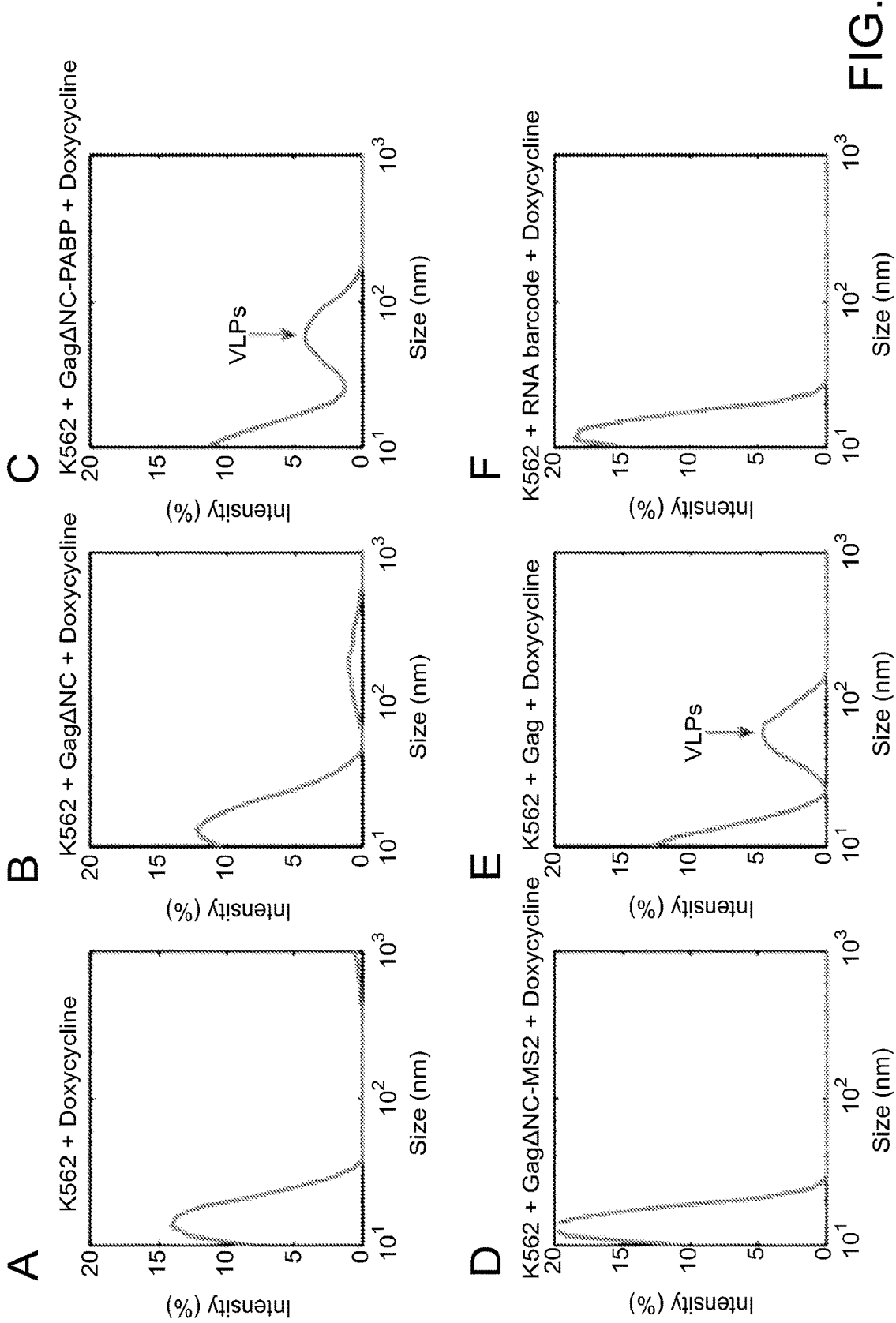
FIG. 14 provides a set of graphs showing detection of inducible VLP constructs and relevant controls.

FIG. 14 show data from experiments using inducible VLP constructs. (A) Wild-type K562 suspension cells show no formation of VLPs, which are expected to have a diameter of roughly 90-120 nm. (B) GagΔNC induction shows no formation of VLPs, this is expected as VLP formation requires RNA binding (Rein et al., 2011). (C) GagΔNC-PABPC4 shows formation of VLPs post induction, as there is a clear secondary peak that is within the range of VLP sizes. (D) GagΔNC-MS2 shows no formation of VLPs. This result is expected, as VLP formation requires RNA binding (Rein et al., 2011). (E) Wild-type Gag shows formation of VLPs, and serves as a positive control. (F) Cells expressing the RNA barcode show no formation of VLPs. Overall, these results (A-F) are as expected.

Example 6—EM Imaging of VLPs

Figure 15:
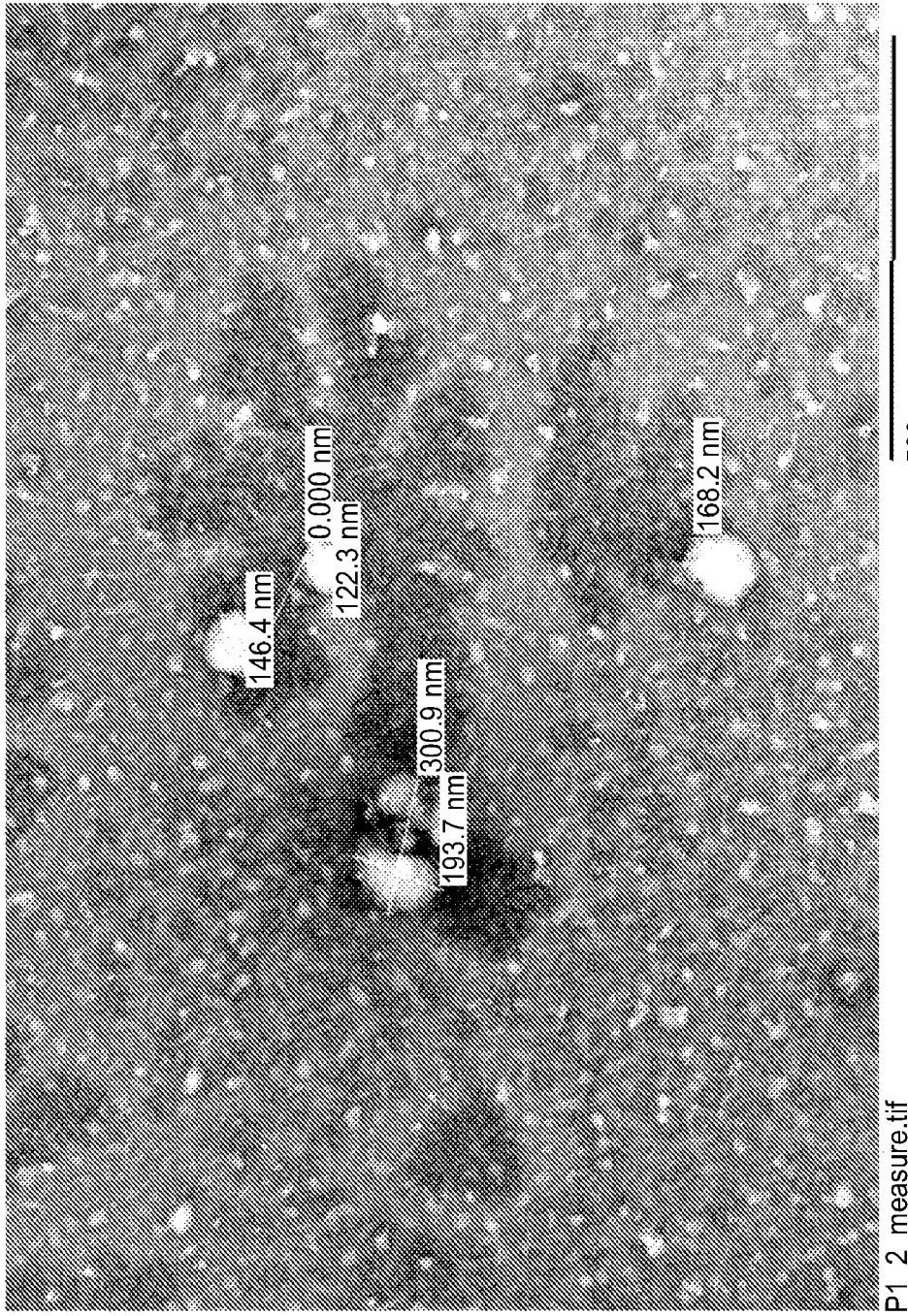
FIG. 15 is an electron micrograph of an example gagΔnc-pabpc4 VLPs collected from K562 cell media.
Figure 16:
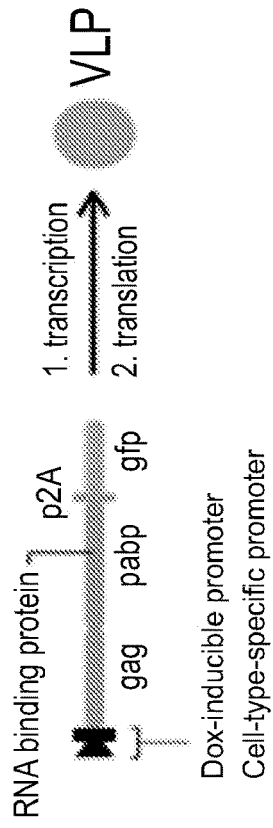
FIG. 16 is a schematic showing an example VLP construct design that includes an affinity tag and the process for the subsequent collection and enrichment of expressed VLPs. VLPs can be captured and purified with affinity-based methods, in order to reduce background analytes, and only capture analytes from cells engineered to self-report.
Figure 16:
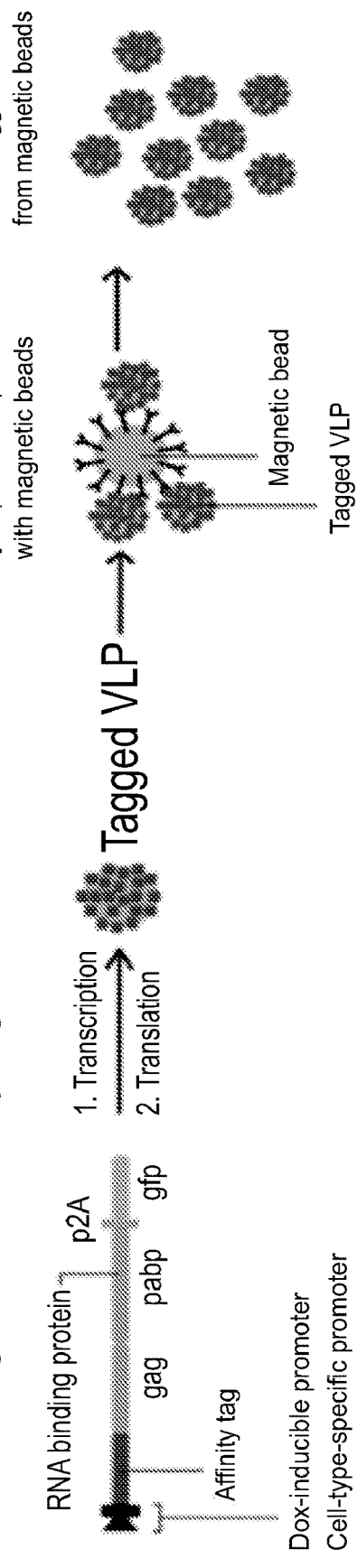
Figure 17:
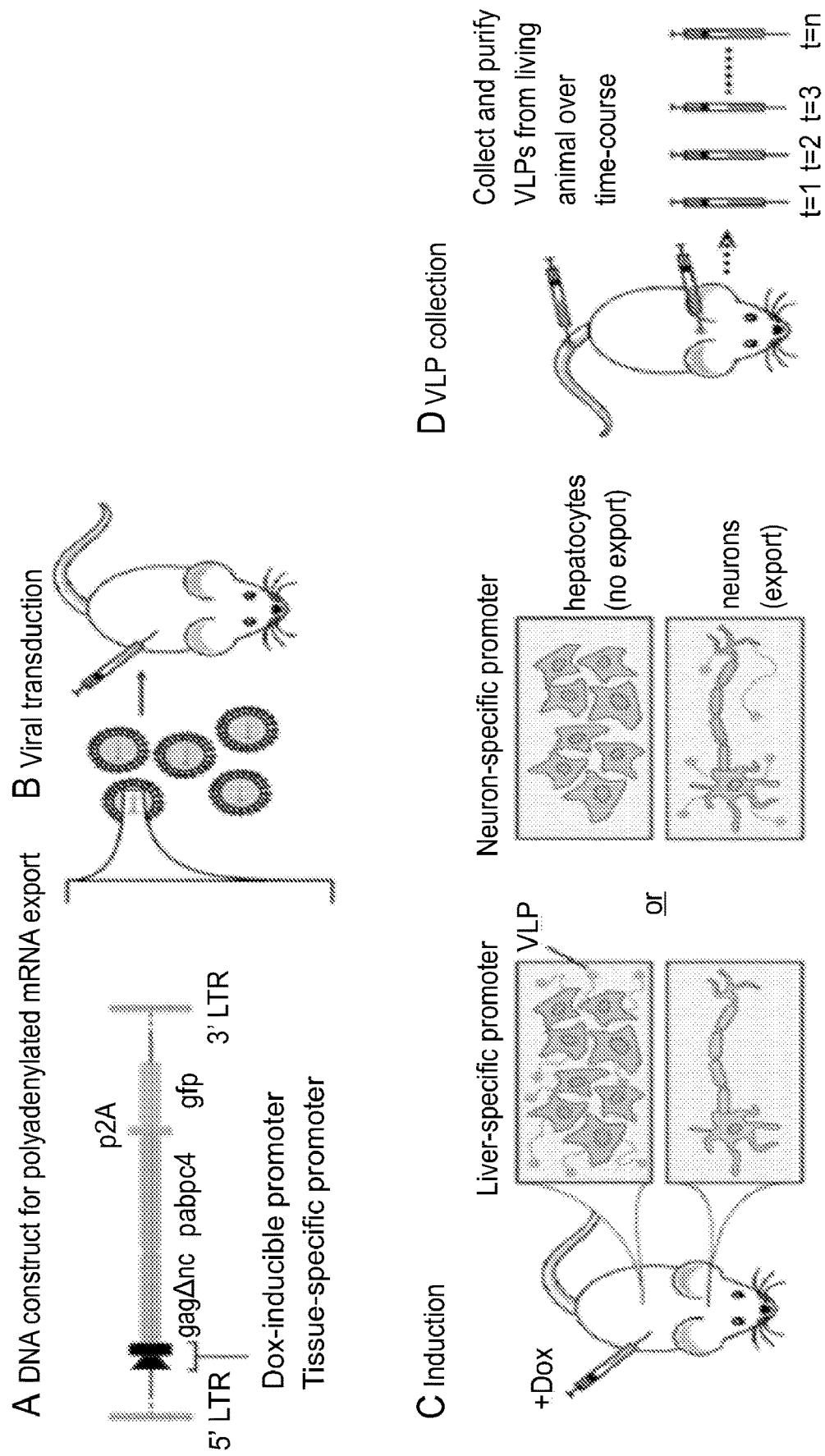
FIG. 17 is a schematic of an example self-reporting VLP construct design. (A) Construct for polyadenylated mRNA export. This construct can be driven by a tissue-specific promoter, a dox-inducible promoter or a combination of the two. A p2A linker is used to allow for translation of a labile GFP reporter. (B) Viral delivery of the construct. The construct can be delivered in vivo by viral transduction (Note: transgenic animals can also be made to carry the construct endogenously). (C) Expression of the construct for self-reporting may begin after proper induction. This is an example of a dox-inducible system coupled with cell-specific promoters. It is expected that the desired cell-type or tissue-type will self-report mRNA via VLPs, while other cell-types and tissue-types will remain unchanged. (D) VLPs can be collected in a variety of ways. Two possible methods are through cerebrospinal fluid (for neural self-reporting) and through tail vein blood collection.

FIG. 15 shows an electron micrograph obtained using transmission electron microscopy on GagΔNC-PABPC4 VLPs. Media was collected from K562 cells with stabile integrations of inducible gagΔnc-pabpc4 (via lentiviral transduction). The collected media was spun at 2000 ref at 4 C to pellet cells and debris. 90% of resulting supernatant was gently collected and filtered with a 0.22 um spin filter (1000 ref for 2 minutes at RT). The resulting filtrate was used for transmission electron microscopy (TEM) with a Joel JEM-1400.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control.

Various modifications and variations of the described methods, pharmaceutical compositions, and kits of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A nucleic acid construct comprising:
a nucleic acid sequence encoding a secretion-inducing protein fused to an affinity domain via a nucleic acid encoding a linker sequence, wherein the affinity domain is selected from the group consisting of: a nucleic acid binding domain and a lipid binding domain, wherein the nucleic acid sequence encoding the secretion-inducing protein comprises SEQ ID NO: 1;
wherein the secretion-inducing protein self-assembles upon expression to form an export compartment that comprises targeted cellular contents that are bound to the affinity domain from live cells; wherein the affinity domain binds lipids or nucleic acids;

wherein the secretion-inducing protein and affinity domain are configured such that upon self-assembly the export compartment comprises a protein layer formed from the secretion-inducing protein and affinity domain whereby the affinity domain is internal to the export compartment so as to package the targeted cellular content that is bound to the affinity domain within the export compartment;

wherein the linker sequence is of a particular size located on the N-terminus or the C-terminus of the secretion-inducing protein, the size of the linker sequence controlling a rate of export, a size of the export compartment, or both.

2. The nucleic acid construct of claim 1, further comprising an inducible promoter to control expression of the secretion-inducing protein.

3. The nucleic acid construct of claim 1, wherein the affinity domain is an albumin, a lipoprotein, a globulin, or peptide.

4. The nucleic acid construct of claim 1, wherein the affinity domain is an apolipoprotein, a scavenger receptor, or a fatty acid binding protein (FABP).

5. The nucleic acid construct of claim 1, wherein the affinity domain is a peptide comprising a DNA-binding domain, an RNA-binding domain, an Argonaute protein or a poly-A binding protein (PABP).

6. The nucleic acid construct of claim 1, wherein the secretion-inducing protein self-assembles to form an export compartment approximately 10 nm to approximately 500 nm in diameter.

7. The nucleic acid construct of claim 1, wherein the construct further comprises an enrichment tag.

8. The nucleic acid construct of claim 7, wherein the enrichment tag comprises Flag, CBP, GST, HA, HBH, MBP, Myc, polyHis, S-tag, SUMO, TAP, TRX or V5.

9. The nucleic acid construct of claim 7, wherein the enrichment tag further comprises a transmembrane domain.

10. The nucleic acid construct of claim 1, wherein the construct further comprises a construct self-reporter molecule; wherein the self-reporter molecule is a detectable reporter molecule.

11. The nucleic acid construct of claim 10, wherein the construct self-reporter molecule is a fluorescent protein.

12. The nucleic acid construct of claim 10, wherein the construct comprises a cleavable linker to facilitate removal of the self-reporter molecule after expression.

13. A vector comprising the nucleic acid construct of claim 1.

14. The vector of claim 13, wherein the vector is a non-viral vector.

15. The vector of claim 13, wherein the vector is a viral vector.

16. A kit comprising the nucleic acid construct of claim 1.

17. A kit comprising the vector of claim 13.

18. A method for continuous monitoring of live cells in vitro comprising:

delivering into one or more cells of the nucleic acid construct of claim 1;

expressing the nucleic acid construct in the one or more cells, wherein expression of the secretion-inducing protein and the affinity domain in the one or more cells results in the export of nucleic acid and lipid cellular contents in association with the secretion-inducing protein, the affinity domain, or both; and isolating the exported nucleic acid and lipid contents at one or more time points.

19. The method of claim 18, wherein the nucleic acid construct is delivered using a non-viral or viral vector.

20. The method of claim 18, wherein the affinity domain is a poly-A-binding protein (PABP) that binds mRNA in the cell.

21. The method of claim 20, further comprising sequencing the isolated mRNA exported from the cell.

22. The nucleic acid construct of claim 11, wherein the fluorescent protein is RFP, YFP, or GFP.

23. The nucleic acid construct of claim 1, wherein the cellular contents are nucleic acids and the nucleic acids are RNA molecules.

24. The nucleic acid construct of claim 23, wherein the RNA molecules are mRNA molecules.

25. The nucleic acid construct of claim 1, wherein the linker sequence is 2-12 amino acids in size.

26. The nucleic acid construct of claim 1, wherein the linker sequence is a $(GS)_n$ linker.

* * * * *

SEQUENCE LISTING

<160> NUMBER OF SEQ ID NOS: 9

<210> SEQ ID NO 1
<211> LENGTH: 1590
<212> TYPE: DNA

<213> ORGANISM: Artificial Sequence
<220> FEATURE:
<223> OTHER INFORMATION: Synthhetic - MLV gag

<400> SEQUENCE: 1

```
atgggccaga ctgttaccac tcccttaagt ttgaccttag gtcactggaa agatgtcgag      60
cggatcgctc acaaccagtc ggtagatgtc aagaagagac gttgggttac cttctgctct     120
gcagaatggc caacctttaa cgtcggatgg ccgcgagacg gcacctttaa ccgagacctc     180
atcacccagg ttaagatcaa ggtctttta cctggcccgc atggacaccc agaccaggtc     240
ccctacatcg tgacctggga agccttggct tttgaccccc ctccctgggt caagcccttt     300
gtacacccta gcctccgcc tcctcttcct ccatccgccc cgtctctccc ccttgaacct     360
cctcgttcga ccccgcctcg atcctccctt tatccagccc tcactccttc tctaggcgcc     420
aaacctaaac ctcaagttct ttctgacagt gggggccgc tcatcgacct acttacagaa     480
gacccccgc cttatagga cccaagacca ccccttccg acaggacgg aaatggtgga     540
gaagcgaccc ctgcgggaga ggcaccggac ccctccccaa tggcatctcg cctacgtggg     600
agacgggagc cccctgtggc cgactccact acctcgcagg cattccccct ccgcgcagga     660
ggaaacggac agcttcaata ctggccgttc tcctcttctg acctttacaa ctggaaaaat     720
aataacccct ttttttctga agatccaggt aaactgacag ctctgatcga gtctgttctc     780
atcacccatc agcccacctg ggacgactgt cagcagctgt ggggactct gctgaccgga     840
gaagaaaaac aacgggtgct cttagaggct agaaaggcgg tgcggggcga tgatgggcgc     900
cccactcaac tgcccaatga agtcgatgcc gcttttcccc tcgagcgccc agactgggat     960
tacaccaccc aggcaggtag gaaccaccta gtccactatc gccagttgct cctagcgggt    1020
ctccaaaacg cgggcagaag cccaccaat ttggccaagg taaaaggaat aacacaaggg    1080
cccaatgagt ctccctcggc cttcctagag agacttaagg aagcctatcg caggtacact    1140
ccttatgacc ctgaggaccc agggcaagaa actaatgtgt ctatgtcttt catttggcag    1200
tctgccccag acattgggag aaagttagag aggttagaag atttaaaaaaa caagacgctt    1260
ggagatttgg ttagagaggc agaaaagatc tttaataaaac gagaaacccc ggaagaaaga    1320
gaggaacgta tcaggagaga aacagaggaa aagaagaaac gccgtaggac agaggatgag    1380
cagaaagaga aagaaagaga tcgtaggaga catagagaga tgagcaagct attggccact    1440
gtcgttagtg gacagaaaca ggatagacag ggaggagaac gaaggaggtc ccaactcgat    1500
cgcgaccagt gtgcctactg caaagaaaag gggcactggg ctaaagattg tccaagaaaa    1560
ccacgaggac ctcgggggacc aagaccgcag                                    1590
```

<210> SEQ ID NO 2
<211> LENGTH: 1935
<212> TYPE: DNA
<213> ORGANISM: Artificial Sequence
<220> FEATURE:
<223> OTHER INFORMATION: Synthetic - PABPC4 - RNA binding protein fragment

<400> SEQUENCE: 2

```
atgaacgctg cggccagcag ctaccccatg gcctccctgt acgtgggcga cctgcattcg      60
gacgtcaccg aggccatgct gtacgaaaag ttcagccccg cggggcctgt gctgtccatc     120
cgggtctgcc gcgatatgat cacccgccgc tccctgggct atgcctacgt caacttccag     180
cagccggccg acgctgagcg ggctttggac accatgaact tgatgtgat taagggaaag     240
```

```
ccaatccgca tcatgtggtc tcagagggat ccctctttga gaaaatctgg tgtgggaaac    300
gtcttcatca agaacctgga caaatctata gataacaagg cactttatga tacttttctc    360
gcttttggaa acatactgtc ctgcaaggtg gtgtgtgatg agaacggctc taagggttat    420
gcctttgtcc acttcgagac caagaggctg ccgacaagg ccatcgagaa gatgaatggc     480
atgctcctca atgaccgcaa agtatttgtg ggcagattca agtctcgcaa agagcgggaa    540
gctgagcttg gagccaaagc caaggaattc accaatgttt atatcaaaaa ctttggggaa    600
gaggtggatg atgagagtct gaaagagcta ttcagtcagt ttggtaagac cctaagtgtc    660
aaggtgatga gagatcccaa tgggaaatcc aaaggctttg ctttgtgag ttacgaaaaa     720 cacgaggatg ccaataaggc tgtggaagag atgaatggaa agaaataag tggtaaaatc     780 atatttgtag gccgtgcaca aaagaaagta gaacggcagg cagagttaaa acggaaattt    840
gaacagttga acaggagag aattagtcga tatcagggg tgaatctcta cattaagaac      900
ttggatgaca ctattgatga tgagaaatta aggaaagaat tttctccttt tggatcaatt    960
accagtgcta aggtaatgct ggaggatgga agaagcaaag ggtttggctt cgtctgcttc   1020
tcatctcctg aagaagcaac caaagcagtc actgagatga atggacgcat tgtgggctcc   1080
aagccactat atgttgccct ggcccagagg aaggaagaga gaaaggctca cctgaccaac   1140
cagtatatgc aacgagtggc tggaatgaga gcacttcctg ccaatgccat cttaaatcag   1200
ttccagcctg cagcgggtgg ctactttgtg ccagcagtcc cacaggctca gggaaggcct   1260
ccatattata cacctaacca gttagcacag atgaggccta atccacgctg gcagcaaggt   1320
gggagacctc aaggcttcca aggaatgcca agtgctatac gccagtctgg gcctcgtcca   1380
actcttcgcc atctggctcc aactgggtct gagtgcccgg accgcttggc tatggacttt   1440 ggtgggctg tgccgccca gcaagggctg actgacagct gccagtctgg aggcgttccc    1500
acagctgtgc agaacttagc gccacgcgct gctgttgctg ctgctgctcc ccgggctgtt   1560 gcccccctaca aatacgcctc cagtgtccgc agccctcatc ctgccataca gcctctgcag   1620
gcaccccagc ctgcggtcca tgtgcagggg caggagccac tgactgcctc catgctggct   1680 gcagcaccc cccaggaaca gaagcagatg ctgggagaac gcttgttccc actcatccaa   1740
acaatgcatt caaatctggc tgggaagatc acgggaatgc tgctggagat agacaactct   1800
gagctgctgc acatgttaga gtcccccgag tctctccgct ccaaggtgga tgaagctgta   1860
gcagttctac aggctcatca tgccaagaaa gaagctgccc agaaggtggg cgctgttgct   1920
gctgctacct cttag                                                    1935

<210> SEQ ID NO 3
<211> LENGTH: 4137
<212> TYPE: DNA
<213> ORGANISM: Artificial Sequence
<220> FEATURE:
<223> OTHER INFORMATION: Synthetic Sequence - dCas9 - RNA binding
      protein fragment

<400> SEQUENCE: 3
atgagcccca agaagaagag aaaggtggag gccagcgaca agaagtacag catcggcctg     60
gccatcggca ccaactctgt gggctgggcc gtgatcaccg acgagtacaa ggtgcccagc    120
aagaaattca aggtgctggg caacaccgac cggcacagca tcaagaagaa cctgatcgga    180
gccctgctgt tcgacagcgg cgaaacagcc gaggccaccc ggctgaagag aaccgccaga    240
agaagataca ccagacggaa gaaccggatc tgctatctgc aagagatctt cagcaacgag    300
```

```
atggccaagg tggacgacag cttcttccac agactggaag agtccttcct ggtggaagag    360
gataagaagc acgagcggca ccccatcttc ggcaacatcg tggacgaggt ggcctaccac    420
gagaagtacc ccaccatcta ccacctgaga aagaaactgg tggacagcac cgacaaggcc    480
gacctgcggt tgatctatct ggccctggcc cacatgatca agttccgggg ccacttcctg    540
atcgagggcg acctgaaccc cgacaacagc gacgtggaca gctgttcat ccagctggtg     600 cagacctaca accagctgtt cgaggaaaac cccatcaacg ccagcggcgt ggacgccaag    660
gccatcctgt ctgccagact gagcaagagc agacggctgg aaaatctgat cgcccagctg    720
cccggcgaga gaagaatgg cctgttcggc aacctgattg ccctgagcct gggcctgacc     780
cccaacttca gagcaacttt cgacctggcc gaggatgcca actgcagct gagcaaggac     840 acctacgacg acgacctgga caacctgctg gcccagatcg cgaccagta cgccgacctg    900 tttctggccg ccaagaacct gtccgacgcc atcctgctga gcgacatcct gagagtgaac    960
accgagatca ccaaggcccc cctgagcgcc tctatgatca agagatacga cgagcaccac    1020
caggacctga ccctgctgaa agctctcgtg cggcagcagc tgcctgagaa gtacaaagag    1080
attttcttcg accagagcaa gaacggctac gccggctaca ttgacggcgg agccagccag    1140
gaagagttct acaagttcat caagcccatc ctggaaaaga tggacggcac cgaggaactg    1200
ctcgtgaagc tgaacagaga ggacctgctg cggaagcagc ggaccttcga caacggcagc    1260 atccccacc agatccacct gggagagctg cacgccattc tgcggcggca ggaagatttt    1320
tacccattcc tgaaggacaa ccgggaaaag atcgagaaga tcctgacctt ccgcatcccc    1380
tactacgtgg cccctctggc caggggaaac agcagattcg cctggatgac cagaaagagc    1440
gaggaaacca tcaccccctg gaacttcgag gaagtggtgg acaagggcgc ttccgcccag    1500
agcttcatcg agcggatgac caacttcgat aagaacctgc ccaacgagaa ggtgctgccc    1560
aagcacagcc tgctgtacga gtacttcacc gtgtataacg agctgaccaa agtgaaatac    1620
gtgaccgagg gaatgagaaa gcccgccttc ctgagcggcg agcagaaaaa ggccatcgtg    1680
gacctgctgt tcaagaccaa ccggaaagtg accgtgaagc agctgaaaga ggactacttc    1740
aagaaaatcg agtgcttcga ctccgtggaa atctccggcg tggaagatcg gttcaacgcc    1800
tccctgggca cataccacga tctgctgaaa attatcaagg acaaggactt cctggacaat    1860
gaggaaaacg aggacattct ggaagatatc gtgctgaccc tgacactgtt tgaggacaga    1920
gagatgatcg aggaacggct gaaaacctat gcccacctgt tcgacgacaa agtgatgaag    1980
cagctgaagc ggcggagata caccggctgg ggcaggctga gccggaagct gatcaacggc    2040
atccgggaca gcagtccgg caagacaatc ctggatttcc tgaagtccga cggcttcgcc    2100
aacagaaact tcatgcagct gatccacgac gacagcctga cctttaaaga ggacatccag    2160
aaagcccagg tgtccggcca gggcgatagc ctgcacgagc acattgccaa tctggccggc    2220
agccccgcca ttaagaaggg catcctgcag acagtgaagg tggtggacga gctcgtgaaa    2280
gtgatgggcc ggcacaagcc cgagaacatc gtgatcgaaa tggccagaga gaaccagacc    2340
acccagaagg gacagaagaa cagccgcgag agaatgaagc ggatcgaaga gggcatcaaa    2400
gagctgggca gccagatcct gaaagaacac cccgtgaaa acacccagct gcagaacgag    2460
aagctgtacc tgtactacct gcagaatggg cgggatatgt acgtggacca ggaactggac    2520
atcaaccggc tgtccgacta cgatgtggac gctatcgtgc ctcagagctt tctgaaggac    2580
gactccatcg acaacaaggt gctgaccaga agcgacaaga accggggcaa gagcgacaac    2640
gtgccctccg aagaggtcgt gaagaagatg aagaactact ggcggcagct gctgaacgcc    2700
```

```
aagctgatta cccagagaaa gttcgacaat ctgaccaagg ccgagagagg cggcctgagc   2760
gaactggata aggccggctt catcaagaga cagctggtgg aaacccggca gatcacaaag   2820
cacgtggcac agatcctgga ctcccggatg aacactaagt acgacgagaa tgacaagctg   2880
atccgggaag tgaaagtgat caccctgaag tccaagctgg tgtccgattt ccggaaggat   2940
ttccagtttt acaaagtgcg cgagatcaac aactaccacc acgcccacga cgcctacctg   3000
aacgccgtcg tgggaaccgc cctgatcaaa agtaccccta agctggaaag cgagttcgtg   3060
tacggcgact acaaggtgta cgacgtgcgg aagatgatcg ccaagagcga gcaggaaatc   3120
ggcaaggcta ccgccaagta cttcttctac agcaacatca tgaactttt caagaccgag    3180 attaccctgg ccaacggcga gatccggaag cggcctctga tcgagacaaa cggcgaaacc   3240
ggggagatcg tgtgggataa gggccgggat tttgccaccg tgcggaaagt gctgagcatg   3300
ccccaagtga atatcgtgaa aaagaccgag gtgcagacag cggcttcag caaagagtct     3360 atcctgccca gaggaacag cgataagctg atcgccagaa agaaggactg ggaccctaag    3420
aagtacggcg gcttcgacag ccccaccgtg gcctattctg tgctggtggt ggccaaagtg   3480
gaaaagggca gtccaagaa actgaagagt gtgaaagagc tgctggggat caccatcatg     3540
gaaagaagca gcttcgagaa gaatcccatc gactttctgg aagccaaggg ctacaaagaa   3600
gtgaaaaagg acctgatcat caagctgcct aagtactccc tgttcgagct ggaaaacggc   3660
cggaagagaa tgctggcctc tgccggcgaa ctgcagaagg aaacgaact ggccctgccc     3720 tccaaatatg tgaacttcct gtacctggcc agccactatg agaagctgaa gggctccccc   3780
gaggataatg agcagaaaca gctgtttgtg aacagcaca agcactacct ggacgagatc     3840
atcgagcaga tcagcgagtt ctccaagaga gtgatcctgg ccgacgctaa tctgacaaa     3900 gtgctgtccg cctacaacaa gcaccgggat aagcccatca gagagcaggc cgagaatatc   3960 atccaccctgt ttaccctgac caatctggga gcccctgccg ccttcaagta ctttgacacc    4020
accatcgacc ggaagaggta caccagcacc aaagaggtgc tggacgccac cctgatccac   4080
cagagcatca ccggcctgta cgagacacgg atcgacctgt ctcagctggg aggcgac      4137
```

<210> SEQ ID NO 4
<211> LENGTH: 66
<212> TYPE: DNA
<213> ORGANISM: Artificial Sequence
<220> FEATURE:
<223> OTHER INFORMATION: Synthetic - p2A protein domain

<400> SEQUENCE: 4

```
ggatccggcg caacaaactt ctctctgctg aaacaagccg agatgtcga agagaatcct      60 ggaccg                                                               66
```

<210> SEQ ID NO 5
<211> LENGTH: 711
<212> TYPE: DNA
<213> ORGANISM: Artificial Sequence
<220> FEATURE:
<223> OTHER INFORMATION: Synthetic - YFP protein domain

<400> SEQUENCE: 5

```
agcaagggcg aggagctgtt caccggggtg gtgcccatcc tggtcgagct ggacggcgac     60
gtaaacggcc acaagttcag cgtgtccggc gagggcgagg gcgatgccac ctacggcaag    120
ctgaccctga agttcatctg caccaccggc aagctgcccg tgccctggcc cacccctcgtg   180
```

```
accaccttcg gctacggcct gcagtgcttc gcccgctacc ccgaccacat gaagcagcac      240
gacttcttca gtccgccat gcccgaaggc tacgtccagg agcgcaccat cttcttcaag       300
gacgacggca actacaagac ccgcgccgag gtgaagttcg agggcgacac cctggtgaac      360
cgcatcgagc tgaagggcat cgacttcaag gaggacggca acatcctggg gcacaagctg     420
gagtacaact acaacagcca caacgtctat atcatggccg acaagcagaa gaacggcatc     480
aaggtgaact tcaagatccg ccacaacatc gaggacggca gcgtgcagct cgccgaccac     540
taccagcaga cacccccat cggcgacggc cccgtgctgc tgcccgacaa ccactacctg      600
agctaccagt ccgccctgag caaagacccc aacgagaagc gcgatcacat ggtcctgctg     660
gagttcgtga ccgccgccgg gatcactctc ggcatggacg agctgtacaa g              711
```

<210> SEQ ID NO 6
<211> LENGTH: 21
<212> TYPE: DNA
<213> ORGANISM: Artificial Sequence
<220> FEATURE:
<223> OTHER INFORMATION: Synthetic - GS6 linker

<400> SEQUENCE: 6

```
ggatcaggat caggatcagg a                                                21
```

<210> SEQ ID NO 7
<211> LENGTH: 204
<212> TYPE: DNA
<213> ORGANISM: Artificial Sequence
<220> FEATURE:
<223> OTHER INFORMATION: Synthetic - bGH pA terminator

<400> SEQUENCE: 7

```
cgactgtgcc ttctagttgc cagccatctg ttgtttgccc ctcccccgtg ccttccttga      60
ccctggaagg tgccactccc actgtccttt cctaataaaa tgaggaaatt gcatcgcatt     120
gtctgagtag gtgtcattct attctggggg gtggggtggg gcaggacagc aaggggagg      180 attgggaaga caatagcagg catg                                             204
```

<210> SEQ ID NO 8
<211> LENGTH: 20
<212> TYPE: DNA
<213> ORGANISM: Artificial Sequence
<220> FEATURE:
<223> OTHER INFORMATION: Synthetic - spacer

<400> SEQUENCE: 8

```
ctgcaggtcg actctagaaa                                                  20
```

<210> SEQ ID NO 9
<211> LENGTH: 25
<212> TYPE: DNA
<213> ORGANISM: Artificial Sequence
<220> FEATURE:
<223> OTHER INFORMATION: Synthetic - Smartseq2 handle

<400> SEQUENCE: 9

```
aagcagtggt atcaacgcag agtac                                            25
```